United States Patent [19]

Stipp et al.

[11] Patent Number: 5,188,858
[45] Date of Patent: Feb. 23, 1993

[54] PROPYLENE GLYCOL DIESTERS OF MEDIUM CHAIN AND LONG CHAIN SATURATED FATTY ACIDS USEFUL AS REDUCED CALORIE COCOA BUTTER SUBSTITUTES AND HARD BUTTERS

[75] Inventors: Gordon K. Stipp, Cincinnati; Bernard W. Kluesener, Harrison, both of Ohio

[73] Assignee: The Procter & Gamble Company, Cincinnati, Ohio

[21] Appl. No.: 644,042

[22] Filed: Jan. 18, 1991

[51] Int. Cl.$^5$ .............. A23L 1/00; A23G 3/00; C09F 5/08

[52] U.S. Cl. .................. 426/531; 426/601; 426/660; 426/804; 554/227

[58] Field of Search .............. 426/601, 602, 603, 604, 426/606, 607, 611, 660, 531; 260/410.6, 410.7

[56] References Cited

U.S. PATENT DOCUMENTS

| | | |
|---|---|---|
| Re. 28,737 | 3/1976 | Yetter . |
| 2,411,567 | 11/1946 | Fisher . |
| 2,520,139 | 8/1950 | Fuchs . |
| 2,655,522 | 10/1953 | Malkemus . |
| 2,924,528 | 2/1960 | Barsky et al. . |
| 2,993,063 | 7/1961 | Alsop et al. . |
| 3,034,898 | 5/1962 | Kuhrt et al. . |
| 3,450,819 | 6/1969 | Babayan et al. . |
| 3,499,917 | 3/1970 | Brandner et al. . |
| 3,989,728 | 9/1972 | Martin . |
| 4,888,196 | 12/1989 | Ehrman et al. ............. 426/601 |
| 5,006,351 | 4/1991 | Klemann et al. . |
| 5,008,126 | 4/1991 | Klemann et al. . |

FOREIGN PATENT DOCUMENTS

| | | |
|---|---|---|
| 760450 | 6/1967 | Canada . |
| 775569 | 1/1968 | Canada . |
| 191217 | 8/1986 | European Pat. Off. . |
| 322027 | 6/1989 | European Pat. Off. . |
| 405873 | 1/1991 | European Pat. Off. . |
| 405874 | 1/1991 | European Pat. Off. . |
| 785933 | 11/1957 | United Kingdom . |

OTHER PUBLICATIONS

Drew Chemical Corp., Propylene Glycol Mono- and Diesters of Fats and Fatty Acids, Food Additive Petition (1962), pp. 00006 to 000037.

Shenai et al, "Structure Property Relationship of Propylene Glycol Diesters," Indian Chem. J. (Jul., 1980), pp. 27–29.

Patwardhan et al, "Short-Chain Fatty Acid Esters of 1,2-Propane Diol," J. Oil Tech. Ass'n. Ind., vol. 6, 1974, pp. 37–39.

Chlebicki et al, "The Reaction of Fatty Acids and Their Derivatives with Propylene Oxide;" A Study of the Reaction of Propylene Glycol Monoesters with Propylene Oxide, Tenside Detergents, vol. 22 (1985), pp. 120–122.

Lewis et al, "Physical Properties of Fatty Acid Esters of 1,2-Propane Diol: 1-Monoesters and Monoacid Diesters," J. Ind. Chem. Soc. vol. 60 (1983), pp. 1062–1064.

Ralston, Fatty Acids and Their Derivatives (1948), pp. 794–803.

Primary Examiner—Joseph Golian
Assistant Examiner—Leslie Wong
Attorney, Agent, or Firm—Eric W. Guttag

[57] ABSTRACT

Reduced calorie 1,2-propylene glycol diesters, where one ester group contains a medium chain $C_6$–$C_{12}$ saturated fatty acid radicals(s), and where the other ester group contains a long chain $C_{20}$–$C_{24}$ saturated fatty acid radical(s) are disclosed. These diesters are preferably obtained by the selective esterification of long chain saturated fatty acid monoesters of propylene glycol with the respective medium chain saturated fatty acids or anhydrides. Certain preferred diesters where the medium chain radicals are $C_8$ and/or $C_{10}$ radicals and where the long chain radicals are $C_{20}$ and/or $C_{22}$ radicals are particularly useful as reduced calorie cocoa butter substitutes and hard butters. Chocolate-flavored products formulated from these preferred diesters, when properly crystallized, are bloom resistant, even when subjected to thermal stress.

42 Claims, 4 Drawing Sheets

PROPYLENE GLYCOL DIESTERS OF MEDIUM CHAIN AND LONG CHAIN SATURATED FATTY ACIDS USEFUL AS REDUCED CALORIE COCOA BUTTER SUBSTITUTES AND HARD BUTTERS

TECHNICAL FIELD

This application relates to novel 1,2-propylene glycol diesters of medium chain and long chain saturated fatty acids and especially their use as reduced calorie cocoa butter substituents and hard butters in flavored confectionery compositions, in particular chocolate-flavored confectionery compositions.

Chocolate derives its desirable eating qualities largely from the melting properties of cocoa butter which is typically present at 25–35% by weight. At room temperature (70°–75° F., 21.1°–23.9° C.) cocoa butter is a firm solid. Firmness is desirable not only to provide "snap" at initial bite, but also to resist deformation and surface marking of the chocolate from time of manufacture to time of consumption.

Above room temperature, cocoa butter melts progressively until it is fully melted near 93°–94° F., (33.9°–34.4° C.), and is therefore entirely liquid below body temperature (98.6° F., 37° C.). This rapid melting at mouth temperature ("mouthmelt") provides a smooth, creamy consistency during eating and insures rapid release of chocolate flavors to the mouth. The relatively sharp melting behavior just a few degrees below body temperature is unique to cocoa butter among natural fats.

The melting behavior of cocoa butter is the result of its unique triglyceride composition. However, this unique triglyceride composition, like the triglyceride composition of other natural fats, is relatively high in calories. Approximately 50% of the calories in chocolate products come from the fat which is exclusively or predominantly cocoa butter. This means that persons who must restrict their intake of calories must either reduce the amount of chocolate products they consume, or in the extreme case, completely exclude such products from their diet. Accordingly, it would be desirable to be able to replace all or a portion of the cocoa butter present in such chocolate products with a substitute fat having fewer calories, while maintaining the desirable physical properties of cocoa butter in chocolate products.

The selection of a reduced calorie substitute fat for cocoa butter is not straightforward. First, the substitute fat must be less efficiently absorbed and/or metabolized by the body in order to exhibit a lower caloric density. Second, the substitute fat should crystallize into a solid form that is very sharp melting and has mouth-melt characteristics the same, or similar, as those of cocoa butter, or combinations of cocoa butter and milkfat, present in confectionery products. Third, the crystalline form of the substitute fat should be stable under typical conditions of confectionery product distribution and handling without any significant change in the mouth-melt characteristics or appearance of the substitute fat-containing confectionery product. Such undesirable changes include the development of a waxy or grainy mouthfeel and the development of bloom, i.e. whitish or gravish discoloration visible on the surface, or sometimes in the interior, of the confectionery product. These changes can be caused by the growth of excessively large fat crystals, the transformation of the fat crystals into a higher melting polymorphic form, the presence of too high a level of lower-melting fatty components, or imcompatibility between the substitute fat and other fats present in the confectionery product, in particular cocoa butter that is typically present in the chocolate liquor and/or cocoa powder used to impart a chocolate flavoring to such products. Fourth, the substitute fat should exhibit controlled shrinkage during cooling for satisfactory molded confectionery product release. Fifth, the substitute fat should be stable towards oxidative rancidity and have a sufficiently neutral flavor such that the flavor properties of the confectionery product are not adversely affected. Lastly, the substitute fat should be processable in current commercial operations used to make confectionery products.

One reduced calorie fat that has been found to be useful as a cocoa butter substitute comprises a fairly high level (e.g., at least about 85%) of combined MML and MLM triglycerides, where M is typically a mixture of $C_8$ and $C_{10}$ saturated fatty acids and L is predominantly behenic acid. See U.S. Pat. No. 4,888,196 to Ehrman et al, issued Dec. 19, 1989. Like cocoa butter, this reduced calorie cocoa butter substitute fat needs to be tempered and crystallized into a stable $\beta$ phase. However, the rate of crystallization of this reduced calorie fat into the $\beta$ phase is too slow to permit processing with equipment typically used with cocoa butter-based chocolate products.

The Ehrman et al patent discloses an alternative tempering process for obtaining flavored confectionery products using this reduced calorie cocoa butter substitute fat. This tempering process involves rapidly cooling the flavored confectionery composition to a temperature of about 57° (13.9° C.) or less so that the reduced calorie cocoa butter substitute fat forms a sub-$\alpha$ phase. This cooled composition is then held at this temperature for a period of time sufficient to form an effective amount of $\beta$-3 crystals from a portion of the sub-$\alpha$ phase of the reduced calorie cocoa butter substitute fat. The cooled composition is then warmed to a temperature in the range of from above about 57° to about 72° F. (about 13.9° to about 22.2° C.) to transform the remaining portion of the reduced calorie cocoa butter substitute fat into the $\beta$-3 phase (the stable $\beta$ form).

Using the tempering scheme disclosed in the Ehrman et al patent, it typically takes from about 1 to about 3 days to obtain chocolate-flavored products which are stable against resulting bloom formation, especially when subjected to thermal stress. In addition, without prolonged tempering according to the Ehrman et al patent, chocolate-flavored confectionery compositions containing these reduced calorie cocoa butter substitute fats can be softer than cocoa butter-based chocolate products, and are therefore more likely to be deformed or marked by standard manufacturing and packaging equipment. Accordingly, there is still a need for a reduced calorie cocoa butter substitute fat that can be more easily adapted to standard manufacturing and packaging equipment used in commercial cocoa butter-based chocolate operations.

BACKGROUND ART

A. Propylene Glycol Diesters Containing Long Chain and Medium Chain Fatty Acids Shenai et al, "*Structure Property Relationship of Propylene Glycol Diester,*" Indian Chem. J. (July, 1980), pp. 27–29, discloses the density and refractive index of a variety of propylene glycol diesters prepared from $C_{12}$–$C_{18}$ fatty acids. See Table 1, which includes the density and refractive index of a propylene glycol diester that was prepared from $C_{12}$ and $C_{18}$ fatty acids. Density and refractive indexes for 31 ether propylene glycol diesters where one of the ester groups contains a $C_{13}$–$C_{19}$ fatty acid radical and where the other ester group contains a $C_4$–$C_{19}$ fatty acid radical, were calculated and then compared to experimental values. See Table 2 which includes the density and refractive indexes of propylene glycol diesters of $C_6$, $C_7$, $C_8$, $C_9$, $C_{10}$, $C_{11}$, or $C_{12}$ fatty acids, and $C_{19}$ fatty acid.

B. Propylene Glycol Diesters Containing Long-Chain Saturated and Unsaturated Fatty Acids Used as Cocoa Butter Substitutes/Hard Butters U.S. Pat. No. 2,993,063 to Alsop et al, issued Jul. 18, 1961, discloses propylene glycol diesters containing a mixture of oleic fatty acid and palmitic/stearic fatty acid radicals, and, optionally minor amounts of other fatty acid radicals such as linoleic, linolenic, lauric and myristic fatty acid radicals. These propylene glycol diesters preferably have melting points of from about 30° to about 35° C. and can be obtained by esterifying propylene glycol with a mixture of the respective acids at 100° to 300° C. (preferably 160° to 260° C.), or by interesterification or trans-esterification of a mixture or blend of the propylene glycol diesters of the individual or mixed fatty acids at 100° to 300° C. in the presence of an alkaline catalyst, e.g. NaOH or KOH.

U.S. Pat. No. 2,924,528 to Barsky et al, issued Feb. 9, 1960, discloses propylene glycol diesters of $C_{16}$ and $C_{18}$ fatty acids useful in hard butter compositions having melting points of about 35° to 40° C. Preferably, these diesters comprise 65 to 85% palmitic acid and 35 to 50% stearic acid, and can optionally include up to 20% oleic acid. These diesters are preferably obtained by esterifying propylene glycol with a mixture of the several acids. See, in particular, Example 1 where a mixture of 57% palmitic acid, 30% stearic acid and 13% oleic acid is used to esterify propylene glycol using powdered zinc as the catalyst at 160° to 170° C., until 75% of the theoretical amount of water is distilled off, at which point the temperature is raised to 230° C.

C. The Esterification of 1-Propylene Glycol Mono-Long Chain Fatty Acid Esters (e.g. 1-Propylene Glycol Monobehenate) With Fatty Acid Anhydrides (e.g. Oleic Anhydride)

U.S. Re. Pat. No. 28,737 to Yetter, reissued Mar. 16, 1976, discloses the reaction of a partial polyol monocarboxylic acid ester with an acidic anhydride in the presence of a perfluoroalkyl sulfonic acid catalyst to produce specific complete mixed polyol esters, especially synthetic cocoa butters, with substantially no ester groups rearrangement. Partial carboxylic acid esters of propylene glycol, such as 1-propylene glycol monostearate or monobenhenate, can be used in this process. These propylene glycol monoesters can be esterified with symmetrical acidic lipid anhydrides of $C_8$–$C_{22}$ fatty acids, e.g. oleic anhydride. Example IX discloses the esterification of 1-propylene glycol monobehenate with oleic anhydride at room temperature using trifluoromethane sulfonic acid as the catalyst. See also U.S. Pat. No. 3,989,728 to Martin, issued Nov. 2, 1972, which has a similar disclosure involving the use of stannic chloride, ferric chloride, zinc chloride or mixtures thereof as the catalyst.

D. Reduced Calorie Fats Based on Triglycerides Containing Medium and Long Chain Saturated Fatty Acids Eurpoean patent application 322,027 to Seiden, published Jun. 28, 1989, discloses reduced calorie fats, comprising MML, MLM, LLM and LML triglycerides, where M is a medium chain saturated ($C_6$–$C_{10}$) fatty acid and where L is a long chain saturated ($C_{17}$–$C_{26}$) fatty acid. In the case of confectionery fats, M is predominantly a $C_8$/$C_{10}$ saturated fatty acid, while L is predominantly behenic acid. These reduced calorie fats are disclosed as being useful in a wide variety of food products, including chocolate-type products, confectionery fillings and other confectioneries, as well as frozen desserts, salad dressings, peanut butter, pre-whipped toppings, frostings, cookies, and cakes.

U.S. Pat. No. 4,888,196 to Ehrman et al, issued Dec. 19, 1989, discloses a tempering process for making chocolate-flavored products containing a reduced calorie cocoa butter substitute fat comprising a fairly high level (e.g., at least about 85%) of combined MML and MLM triglycerides, where M is typically a mixture of $C_8$ and $C_{10}$ saturated fatty acids and L is predominantly behenic acid.

DISCLOSURE OF THE INVENTION

The present invention relates to certain reduced calorie 1,2-propylene glycol diesters, as well as selective processes for making these diesters, the use of these diesters in flavored reduced calorie confectionery products, and processes for making boom-resistant confectionery products containing these diesters. In the propylene glycol diesters of the present invention, one ester group contains a medium chain $C_6$–$C_{12}$ (preferably a less caloric $C_8$ and/or $C_{10}$) saturated fatty acid radical, or mixture thereof, while the other ester group contains a poorly absorbed long chain $C_{20}$–$C_{24}$ (preferably $C_{20}$ and/or $C_{22}$) saturated fatty acid radical, or mixture thereof. These preferred propylene glycol diesters exhibit a 40-60% lower caloric density compared to normal confectionery fats (e.g., cocoa butter), typically have peak melt points (as measured by Differential Scanning Calorimetry) in the range of from about 27° to about 45° C., and are very sharp-melting, i.e. melt over a narrow temperature range of from about 3° to about 5° C. Certain preferred propylene glycol diester compositions of the present invention (i.e., medium chain radicals are predominantly a mixture of $C_8$ and $C_{10}$ radicals and long chain radicals are predominantly a mixture of $C_{20}$ and $C_{22}$ radicals) have peak melt points in the range of from about 27° to about 37° C. and are particularly useful as reduced calorie cocoa butter substitutes and hard butters in flavored confectionery products, especially in chocolate-flavored products.

A particularly desirable property of the preferred propylene glycol diester compositions of the present invention is that they can crystallize rapidly into a stable $\beta'$ solid form. The crystallization properties of these preferred propylene glycol diester compositions are similar to commercial hard butters or cocoa butter substitutes in solidifying from a melted state directly into a stable $\beta'$ form without the need of prolonged tempering to control complex fat polymorphism, as in the case of the reduced calorie cocoa butter substitute fats disclosed in the Ehrman et al patent. Accordingly, chocolate-flavored products containing these preferred propylene glycol diester compositions can be easily handled by standard manufacturing and packaging equipment used with hard butter or cocoa butter-based chocolate products. The resultant finished confectionery products containing these preferred propylene glycol diester compositions exhibit a moderate brittleness peculiar to cocoa butter, yet have no plasticity at ambient temperatures and have good surface luster free of fat bloom.

Other desirable properties of these preferred propylene glycol diester compositions include: (a) good chocolate flavor release from the confectionery products; (b) good flow characteristics (i.e. reduced yield value) during processing of confectionery formulations at lower fat contents than are possible with cocoa butter-based formulations; (c) the ability to tolerate relatively high levels of milkfat and/or cocoa butter in confectionery formulations; (d) a high heat of fusion that imparts desirable mouth-cooling effects; (e) good mold release, gloss and "snap" in chocolate-flavored products; (f) a bland, neutral flavor that allows formulation flexibility in chocolate-flavored products; (g) high stability to oxidation since these diester compositions contain minimal/zero levels of unsaturated fatty acids; (h) confectionery products having resistance to scuffing and bloom formation when properly crystallized, even when subjected to thermal stress.

A. BRIEF DESCRIPTION OF THE DRAWINGS

FIG. 1 is a graphical representation of the $\beta'$ phase peak melt points, as determined by Differential Scanning Calorimetry (DSC), of relatively pure propylene glycol diester compositions according to the present invention having four different levels of $C_{20}$ and $C_{22}$ long chain saturated fatty acid radicals, where the weight ratio of medium chain saturated fatty acid radicals is varied from all $C_8$ (caprylic) to all $C_{10}$ (capric) radicals.

B. DEFINITIONS

Figure 1:
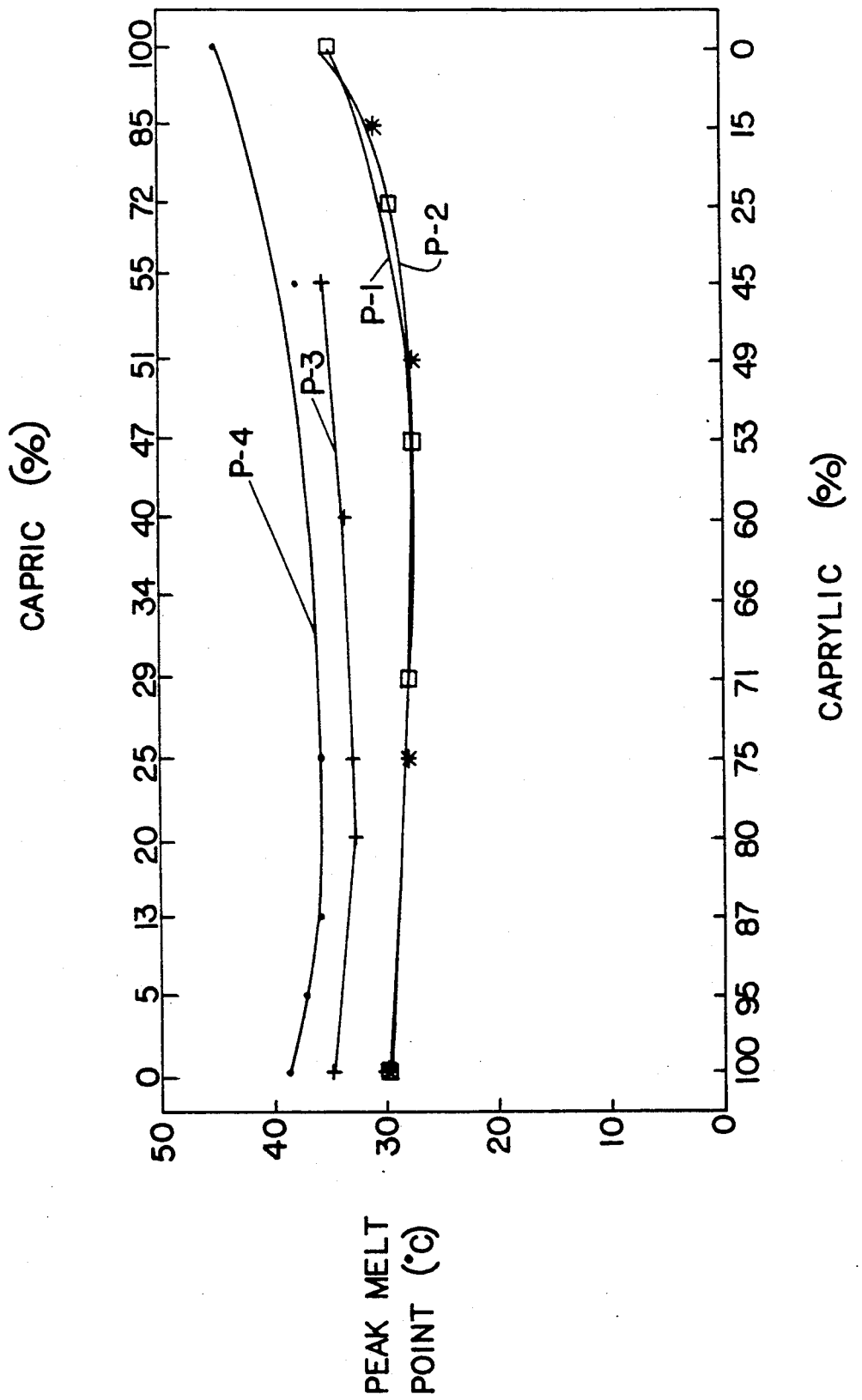

The terms "1,2-propylene glycol" and "propylene glycol" are used interchangeably herein to refer to the propanediol having hydroxy groups at the #1 and #2 positions.

By "medium chain fatty acid," as used herein, is meant a natural or synthetic fatty acid, or mixture thereof, having 6 to 12 carbon atoms.

By "medium chain saturated fatty acid," as used herein, is meant $C_6$ (caproic), $C_8$ (caprylic), $C_{10}$ (capric), or $C_{12}$ (lauric) saturated fatty acids, or mixtures thereof. The $C_7$, $C_9$ and $C_{11}$ saturated fatty acids are not commonly found, but they are not excluded from the possible medium chain fatty acids.

By "medium chain fatty acid anhydride," as used herein, is meant the dehydration product of two medium chain fatty acids.

By "long chain fatty acid," as used herein, is meant a natural or synthetic fatty acid, or mixture thereof, having 20 to 24 carbon atoms.

By "long chain saturated fatty acid," as used herein, is meant $C_{20}$ (arachidic), $C_{21}$ (heneicosanoic), $C_{22}$ (behenic), $C_{23}$ (tricosanic), or $C_{24}$ (lignoceric) saturated fatty acids, or mixtures thereof.

By "ML", as used herein, is meant a propylene glycol diester containing a long chain fatty acid residue in the #2 position and a medium chain fatty acid residue in the #1 position, while "LM" represents a propylene glycol diester with a long chain fatty acid residue in the #1 position and a medium chain fatty acid residue in the #2 position. Similarly, "MM" represents a propylene glycol diester containing medium chain fatty acid residues at both positions, while "LL" represents a propylene glycol diester containing long chain fatty acid residues at both positions.

By "long chain fatty acid monoester of propylene glycol" is meant a monoester of propylene glycol which contains one long chain fatty acid residue in the #1 position (i.e. a 1-monoester) or the #2 position (i.e. a 2-monoester).

As used herein, the term "comprising" means various components or steps can be conjointly employed in the present invention. Accordingly, the term "comprising" encompasses the more restrictive terms "consisting essentially of" and "consisting of."

The "$\beta'$" and "$\beta$" phases referred to herein are crystalline fat phases well known to those skilled in the art of fat X-ray crystallography. See Wille et al "Polymorphism of Cocoa Butter," *J. Am. Oil Chem. Soc.*, Vol. 43 (1966), pp. 491–96, which describes the six crystalline fat phases of cocoa butter.

All percentages, ratios and proportions used herein are by weight unless otherwise specified.

C. Propylene Glycol Diesters

The propylene glycol diesters that are useful in the present invention involve a combination of two different ester groups: (a) one containing a medium chain ($C_6$–$C_{12}$) saturated fatty acid radical(s); and (b) the other containing a long chain ($C_{20}$–$C_{24}$) saturated fatty acid radical(s). Preferably, the medium chain radicals are predominantly (e.g., at least about 90%, most preferably at least about 95%) $C_8$ and/or $C_{10}$ saturated fatty acid radicals, while the long chain radicals are predominantly (e.g., at least about 85%, most preferably at least about 90%) $C_{20}$ and/or $C_{22}$ saturated fatty acid radicals. The medium chain and long chain saturated fatty acid radicals of these propylene glycol diesters can be single fatty acid radical species, e.g., diesters of $C_8$ and $C_{20}$, $C_8$ and $C_{22}$, $C_{10}$ and $C_{20}$, or $C_{10}$ and $C_{22}$, saturated fatty acid radicals, or else a mixture of medium chain saturated fatty acid radicals and/or a mixture of long chain saturated fatty acid radicals, e.g., a mixture of diesters having $C_8$ and $C_{20}$ saturated fatty acid radicals, $C_8$ and $C_{22}$ saturated fatty acid radicals, $C_{10}$ and $C_{20}$ saturated fatty acid radicals, and $C_{10}$ and $C_{22}$ saturated fatty acid radicals. In addition, these propylene glycol diesters can be single isomers, i.e., the ML or LM isomers, or more typically mixtures of ML and LM isomers.

The propylene glycol diesters involving combinations of medium chain $C_8$ and/or $C_{10}$ saturated fatty acid radicals and long chain $C_{20}$ and/or $C_{22}$ saturated fatty acid radicals typically have $\beta'$ phase peak melt points in the range of from about 27° to about 45° C., as measured by Differential Scanning Calorimetry (DSC). The peak melt points of relatively pure (i.e. 98–99.5% purity) propylene glycol diesters having four different levels of $C_{20}/C_{22}$ saturated fatty acid radicals of 43%/46% (P-1), 36%/56% (P-2), 7%/86% (P-3) and 2%/93% (P-4), and where the weight ratio of medium chain fatty acid radicals is varied from all $C_8$ (caprylic) to all $C_{10}$ (capric) radicals, are shown in the following table:

| $C_8$ to $C_{10}$ weight ratio (%) | Peak Melt Points (°C.) | | | |
|---|---|---|---|---|
| | P-1 | P-2 | P-3 | P-4 |
| 100:0 | 29.6 | 29.9 | 34.6 | 38.5 |
| 95:5 | — | — | — | 37.0 |
| 87:13 | — | — | — | 35.5 |
| 80:20 | — | — | 32.5 | — |
| 75:25 | — | 27.9 | 32.8 | 35.6 |
| 71:29 | 27.5 | — | — | — |
| 66:37 | — | — | — | 36.5 |
| 60:40 | — | — | 33.3 | — |
| 53:47 | 27.1 | — | — | — |
| 49:51 | — | 27.4 | — | — |
| 45:55 | — | — | 35.2 | 37.5 |
| 25:75 | 29.1 | 29.0 | — | — |
| 15:85 | — | 30.6 | — | — |
| 0:100 | 34.3 | 35.1 | — | 44.7 |

The peak melt points for the propylene glycol diesters shown in the above table are graphically portrayed as peak melt point curves P-1, P-2, P-3 and P-4 in FIG. 1. As shown in the above table, the propylene glycol diesters of the present invention typically contain a mixture of medium chain saturated fatty acid radicals and/or a mixture of long chain saturated fatty acid radicals. As shown in FIG. 1, it has been surprisingly found that the resulting mixtures of propylene glycol diesters form eutectics. In particular, adjustments in the weight ratio of long chain arachidic ($C_{20}$) and behenic ($C_{22}$) saturated fatty acid radicals can be used to significantly shift higher or lower the peak melt point curves of the resulting propylene glycol diesters. Compare peak melt point curves P-1 and P-2 with peak melt point curves P-3 and P-4 shown in FIG. 1. As also shown in FIG. 1, adjustments in the weight ratio of medium chain caprylic ($C_8$) and capric ($C_{10}$) fatty acid radicals can be used to vary more modestly the peak melt points of the resulting propylene glycol diesters.

The unexpected ability to form eutectic mixtures by adjusting the weight ratios of medium chain fatty acid radicals, and particularly the weight ratios of long chain fatty acid radicals, is especially important in providing propylene glycol diester compositions having certain melting properties. For example, fat compositions useful as cocoa butter substitutes or hard butters need to have peak melt points in the range of from about 27° to about 37° C., and preferably from about 29° to about 35° C. Compositions of the present invention having such melting properties comprise propylene glycol diesters wherein the medium chain saturated fatty acid radicals comprise from 0 to 100% (preferably from about 25 to 100%) caprylic ($C_8$) fatty acid radicals, and from 0 to 100% (preferably from 0 to about 75%) capric ($C_{10}$) fatty acid radicals; and wherein the long chain saturated fatty acid radicals comprise from about 30 to about 95% (preferably from about 50 to about 90%) behenic ($C_{22}$) fatty acid radicals, from about 5 to about 70% (preferably from about 10 to about 50%) arachidic ($C_{20}$) fatty acid radicals, and from 0 to about 5% (preferably from 0 to about 3%) lignoceric ($C_{24}$) fatty acid radicals. These preferred propylene glycol diester compositions can be obtained directly by synthesis methods to be described hereafter, by blending pure propylene glycol diesters of single species or by bleeding various mixtures of propylene glycol diesters.

Figure 2:
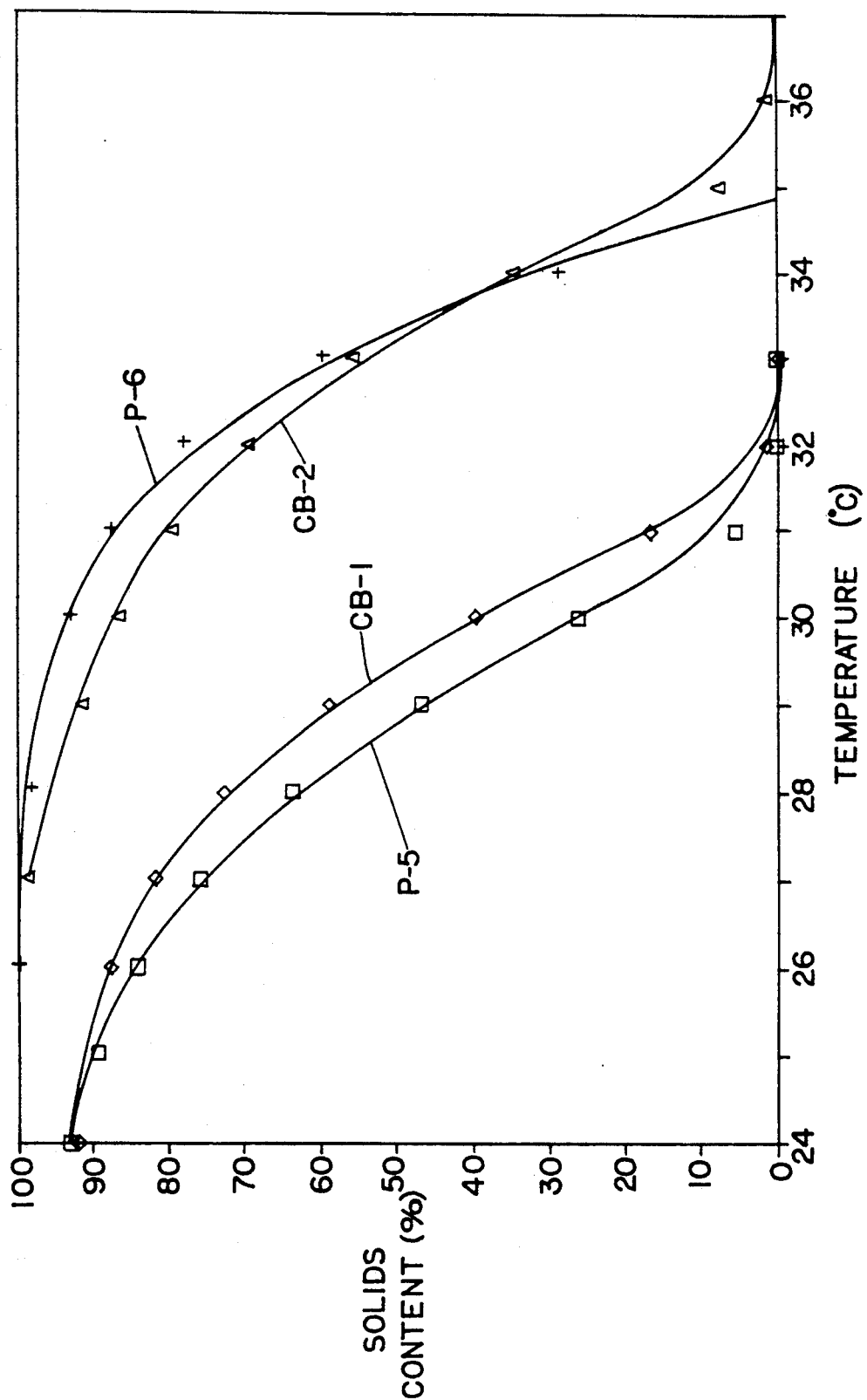
FIG. 2 is a graphical representation of the solids content curves, as determined by DSC, of fully tempered Brazilian and West African cocoa butters, as well as the stable $\beta'$ phase of the propylene glycol diester compositions of Examples 1 and 5C.

The propylene glycol diesters of the present invention can be tailored to provide different melting profiles, including melting profiles similar to cocoa butter. FIG. 2 graphically portrays the solids content curves of the stable $\beta'$ phase of the propylene glycol diester composition of Example 1 (P-5), a fully tempered Brazilian cocoa butter (CB-1), the stable $\beta'$ phase of the propylene glycol diester composition of Example 5C (P-6), and a fully tempered West African cocoa butter (CB-2). The curves shown in FIG. 2 are based on solids content values determined by DSC at various temperatures and are shown in the following table:

| °C. | Solids Content (%) | | | |
|---|---|---|---|---|
| | P-5 | CB-1 | P-6 | CB-2 |
| 24 | 92.6 | 91.6 | — | — |
| 25 | 89.3 | — | — | — |
| 26 | 84.1 | 87.7 | 99.7 | — |
| 27 | 75.8 | 81.8 | — | 98.7 |
| 28 | 63.7 | 72.7 | 97.9 | — |
| 29 | 46.9 | 58.9 | — | 91.4 |
| 30 | 26.2 | 39.7 | 93.1 | 86.8 |
| 31 | 5.5 | 16.8 | 87.7 | 79.7 |
| 32 | 0.1 | 1.4 | 77.9 | 69.8 |
| 33 | 0 | 0 | 59.8 | 56.0 |
| 34 | — | — | 28.7 | 34.9 |
| 35 | — | — | 0 | 7.5 |
| 36 | — | — | — | 1.3 |
| 37 | — | — | — | 0.5 |
| 38 | — | — | — | 0 |

As shown in FIG. 2, the melting profile of the propylene glycol diester composition of Example 1 (P-5) is similar to that of a Brazilian cocoa butter (CB-1). As also shown in FIG. 2, the melting profile of the propylene glycol diester composition of Example 5C (P-6) is similar to that of a West African cocoa butter (CB-2).

Because of the way the propylene glycol diesters of the present invention are typically synthesized, these propylene glycol diester compositions usually comprise not only ML/LM diesters, but also MM and LL diesters. The inclusion of higher levels of MM diesters tend to make the resulting propylene glycol diester compositions softer (i.e. by reducing the amount of solids present). The inclusion of higher levels of LL diesters tends to make the resulting propylene glycol diester compositions harder and more waxy-tasting. When used as cocoa butter substitutes or hard butters, the propylene glycol diester compositions of the present invention comprise at least about 90% (preferably at least about 95%, most preferably at least about 98%) ML/LM diesters, up to about 10% (preferably up to about 2.5%, most preferably up to about 1%) MM diesters, and up to about 10% (preferably up to about 2.5% most preferably up to about 1%) LL diesters.

In addition to maximizing the level of ML/LM diesters, the preferred propylene glycol diester compositions of the present invention have minimized levels of unesterified (free) long chain (L) saturated fatty acids. High levels of unesterified long chain fatty acids can promote bloom formation and can impart waxy mouthfeel impressions in the resulting chocolate-flavored product. The level of unesterified long chain saturated fatty acids in such compositions is preferably about 1% or less, more preferably about 0.5% or less and most preferably about 0.1% or less.

A particularly desirable property of these preferred propylene glycol diester compositions is that they can rapidly crystallize into a stable, solid $\beta'$ phase without the need of prolonged tempering. These preferred propylene glycol polyester compositions also have a relatively high solids level (e.g., from about 80 to about 99.7% solids as measured by DSC) at ambient temperatures (e.g., from about 15° to about 25° C.) so as to be firm and solid (i.e., not plastic). Surprisingly, these preferred propylene glycol diester compositions are compatible with cocoa butter at levels of up to at least about 15%, and with milkfat/butterfat at levels of up to at least about 25%. Other desirable properties of these preferred propylene glycol diester compositions include: (1) a relatively bland flavor that permits greater formulation flexibility; (2) good chocolate flavor release in formulated products; (3) when properly crystallized, good "snap", good mold release, resistance to scuffing, very high gloss and good bloom stability, even when subjected to thermal stress; (4) good flow characteristics during processing of confectionery formulations at lower fat contents than is possible with cocoa butter-based formulations; and (5) a high heat of fusion that imparts desirable cooling sensations in the mouth.

D. Methods for Making Propylene Glycol Diesters

Propylene glycol diesters useful in the present invention can be synthesized by a variety of methods. These synthesis methods include the following:

(a) esterification of propylene glycol with the respective fatty acids, fatty acid anhydrides or acyl chlorides;

(b) transesterification of propylene glycol diesters with the lower alkyl ($C_1$-$C_3$) esters of the respective fatty acids;

(c) acidolysis of propylene glycol diesters with the respective fatty acids;

(d) random rearrangement of mixed propylene glycol diesters; and (e) combinations of methods (a) through (d), for example, by transesterification of propylene glycol with a source oil of long chain fatty acids to make the respective monoesters of propylene glycol, followed by esterification or transesterification with a source of medium chain fatty acids.

A preferred process for obtaining higher levels of the desired ML/LM propylene glycol diesters involves the selective esterification of long chain (saturated) fatty acid monoesters of propylene glycol with the respective medium chain (saturated) fatty acids or fatty acid anhydrides. (This preferred process is "selective", relative to random esterification processes, in enhancing the level of desired ML/LM diesters obtained.) The source of medium chain fatty acids or fatty acid anhydrides used in this preferred process needs to be of sufficiently high purity to provide the desired level of ML/LM propylene glycol diesters. When medium chain fatty acids are used in this preferred method, the source of medium chain fatty acids is at least about 90% pure medium chain fatty acids, and is preferably at least about 95% pure, in such acids. When fatty acid anhydrides are used in this preferred process, the source of medium chain fatty acid anhydrides is at least about 50% pure medium chain fatty acid anhydrides, with up to about 50% of the balance being medium chain fatty acids. (Due to the very fast acylation rate of the anhydrides versus the acids, the medium chain fatty acids are essentially an inert diluent under the reaction conditions used in this preferred process.) Preferably the source of medium chain fatty acid anhydrides is at least about 70% pure in such fatty acid anhydrides, with up to about 30% of the balance being typically medium chain fatty acids.

The medium chain fatty acids useful in this preferred process can be derived from a number of different sources. For example, medium chain saturated fatty acids can be obtained from natural sources such as coconut, palm kernel or babassu oils, or from synthesized medium chain triglycerides, such as the Captex 300 brands sold by Capital City Products of Columbus, Ohio. Typically, these sources of medium chain fatty acids are subjected to hydrolysis to provide a mixture of free fatty acids, followed by fractionational distillation to provide a fatty acid fraction enriched in the medium chain fatty acids. For example, refined, bleached, and deodorized coconut or palm kernel oil, which has been hydrogenated to further increase the level of saturated fatty acids, can be subjected to hydrolysis conditions, followed by fractionational distillation to provide a fatty acid fraction enriched in a mixture of $C_8$ and $C_{10}$ saturated fatty acids that is typically processed to meet Food Chemical Codex criteria for caprylic ($C_8$) and capric ($C_{10}$) acids. It is also desirable that the sources of medium chain fatty acids have good thermal color stability, e.g., after heating at 205° C. for 2 hours, a mixture of $C_8$ and $C_{10}$ saturated fatty acids has only a 5-10% optical transmission reduction when measured at 440/550 nanometers.

The medium chain fatty acid anhydrides useful in this preferred process can also be derived from a number of difference sources. For example, medium chain fatty acid anhydrides can be obtained commercially from Sigman Aldrich Chemicals of St. Louis, Mo. They can also be synthesized from a variety of dehydration agents (e.g. $P_2O_5$, phosgene, activated alumina, acetic anhydride, etc.) and the appropriate fatty acid(s), fatty acid lower alkyl ($C_1$-$C_3$) ester(s), or combinations thereof. See U.S. Pat. No. 2,520,139 to Fuchs, issued Aug. 29, 1950; U.S. Pat. No. 2,411,567 to Fisher, issued Nov. 26, 1946; and Ralston, *Fatty Acids and Their Derivatives* (1948), pp. 794–803, which are all incorporated by reference.

The medium chain fatty acid anhydrides useful in this preferred process are typically prepared by thermal dehydration of the corresponding medium chain fatty acids with a stoichiometric amount or excess of acetic anhydride, followed by separation of the desired medium chain fatty acid anhydrides from the resulting reaction mixture. A preferred synthesis for preparing these medium chain fatty acid anhydrides involves dehydration with acetic anhydride either at low temperatures (e.g., 0° to 60° C.) using strong acid catalysts (e.g., perchloric acid), or at high temperatures (e.g., from 120° to 175° C.) without the use of strong acid catalysts, but with volatilization or stripping of the acetic acid formed during the reaction. Lower reaction temperatures and shorter reaction times are usually preferred to minimize the formation of medium chain di-fatty ketones (e.g., pentadecanone). Typically, the medium chain fatty acid is heated with a 0 to 200% mole excess of acetic anhydride under reflux to effect this dehydration reaction. The acetic acid formed, plus any residual unreacted acetic anhydride, is distilled off at a temperature of from 140° to 175° C. under reduced pressure (e.g., 200 mm. Hg). This dehydration reaction can be conducted in either batch or continuous reaction/stripping systems. When stoichiometric amounts of acetic anhydride are used, the reaction mixtures obtained typically comprise from about 60 to about 80% symmetrical (e.g., $C_8/C_8$, $C_{10}/C_{10}$ or $C_8/C_{10}$) fatty acid anhydrides, from about 15 to about 30% fatty acids, and from about 5 to about 10% mixed, asymmetrical (e.g., $C_2/C_8$ or $C_2/C_{10}$) fatty acid anhydrides.

Any asymmetrical fatty acid anhydrides that are present in the reaction mixture are unstable at temperatures above about 200° C., and are therefore readily converted to symmetrical fatty acid anhydrides by high temperature distillation (e.g., for 15 minutes at 205°-225° C. and at reduced pressure). Distillation is continued until the residual levels of the combined acetic impurities (e.g., acetic acid, acetic anhydride and asymmetrical fatty acid anhydrides containing acetyl ($C_2$) groups) are reduced to about 0.5% or less, preferably to about 0.1% or less. This reduction in acetic impurities is necessary to minimize the formation of acetin esters during subsequent esterification.

The completeness of the dehydration reaction is a function of reaction time and acetic anhydride level. As a result, the ultimate yield of the desired medium chain fatty acid anhydrides is achieved in very short reaction times, and is not changed unless the equilibrium is shifted by removal of the acetic acid formed. The ultimate yield of medium chain fatty acid anhydride is primarily determined by the amount of excess acetic anhydride used. This ultimate yield reaches a level of from 85 to 95% when a from 50 to 100% mole excess of acetic anhydride is used. This ultimate yield can be increased to from 95 to 98% by using a from 100 to 200% mole excess of acetic anhydride.

The long chain fatty acid monoesters of propylene glycol useful in this preferred process can be prepared by a wide variety of techniques. These techniques include:

(a) esterification or transesterification of propylene glycol with the respective long chain fatty acid(s), long chain fatty acid lower alkyl ($C_1$-$C_3$) ester(s), or long chain fatty acid glyceride(s), optionally using strong base esterification catalysts such as sodium metal or sodium methoxide, or strong acid esterification catalysts such as p-toluenesulfonic acid or cationic exchange resins such as Amberlite IR-120 (H+). See U.S. Pat. No. 3,034,898 to Kuhrt et al, issued May 15, 1962, and Canadian patent 775,569 to Schmadeke, issued Jan. 9, 1968 (use of strong base esterification catalysts), and Canadian Patent 760,450 to Swicklik, issued Jun. 6, 1967 (use of strong acid esterification catalysts), which are all incorporated by reference;

(b) esterification of transesterification of propylene glycol with the respective long chain fatty acid(s) or long chain fatty acid lower alkyl ester(s) using a monoglyceride lipase (e.g., Ammano Pharmaceutical Type G) followed by purification. Cf. European patent application 191,217 to Yamaguchi et al, published Aug. 20, 1986 (preparation of monoglycerides using such lipases) which is incorporated by reference;

(c) reaction of 1,2-propylene oxide with the respective long chain fatty acid(s) in the presence of a basic or acidic catalyst. See U.S. Pat. No. 3,499,917 to Brandner et al, issued Mar. 10, 1970, and Chlebicki et al, "The Reaction of Fatty Acids and Their Derivatives with Propylene Oxides," Parts 1 and 2, *Tenside Detergents*, Vol. 22 (1985), pp. 117-22, which are incorporated by reference.

The long chain fatty acids per se or naturally occurring fats and oils can serve as sources of the long chain fatty acids. For example, high erucic acid rapeseed oil, certain hydrogenated marine oils, such as sardine, herring and menhaden oil, and meadowfoam (Lymnanthes alba) oil, when hydrogenated to an I.V. of about 2 or less, are suitable sources of long chain ($C_{20}$-$C_{24}$) saturated fatty acids. Alternatively, mixed chain length fatty acid monoesters of propylene glycol can be fractionated to provide a source of long chain fatty acid monoesters. For example, hydrogenated high erucic acid rapeseed oil can be transesterified with propylene glycol to provide a mixture of long chain fatty acid monoesters of glycerol and propylene glycol which can be subsequently fractionated by crystallization, liquid/liquid extraction or adsorptive separation to yield a behenic acid-enriched mixture of propylene glycol monoesters.

For the preferred process of the present invention, the source of long chain fatty acid monoesters of propylene glycol needs to be of sufficiently high purity in order to provide the desired level of ML/ML diesters. Generally, the source of these monoesters needs to be at least about 75% pure in long chain fatty acid monoesters of propylene glycol, and is preferably at least about 90% pure, most preferably at least about 98% pure, in such monoesters. Such purities can typically be achieved by purification of the crude source of monoesters by molecular distillation, fractional crystallization, liquid/liquid extraction or adsorptive separation, e.g., by weak acid ion exchange resins to remove various impurities, and, particularly, to decrease the level of long chain fatty acids to about 0.5% or less. Residual propylene glycol present in the crude source of monoesters can be removed by settling, centrifugation, thermal distillation, inert gas stripping, or fractional crystallization to decrease the propylene glycol level to about 0.5% or less. The preferred source of monoesters for use in the preferred process of the present invention is in at least about 90%, most preferably in at least about 95%, pure mixture of propylene glycol monobehenate and propylene glycol monoarachidate, wherein the weight ratio of monobehenate to monoarachidate is from about 95:5 to about 30:70.

An example of a process for making long chain fatty acid monoesters of propylene glycol according to the present invention is as follows: a mixture of long chain fatty acid(s) and propylene glycol in a 1:2 to 1:4 mole ratio is formed. This mixture is heated without catalyst at 175°-200° C. under reflux. Alternatively, the reaction mixture can be heated at higher temperatures (e.g., 200°-300° C.), under pressure (e.g., 5-100 psi) and without catalyst, to facilitate the reaction rate. See U.S. Pat. No. 2,655,522 to Malbeams, issued Oct. 13, 1953. During the reaction, water is removed by use of nitrogen or a vacuum. Because the separation of unesterified long chain fatty acids from propylene glycol monoesters is difficult, it is important that the reaction be carried out to completion. Accordingly, the reaction is carried out until the acid value of the reaction mixture is less than about 5. At this point, an equilibrium is achieved wherein the mixture typically contains at least ⅔ monoester and up to ⅓ diester. The propylene glycol in this reaction mixture is then separated by vacuum, evaporation, stripping or settling. The desired monoesters are then distilled from the reaction mixture using molecular thin film distillation; the residual components can be recycled for further reaction.

In the preferred process of the present invention, the long chain fatty acid monoesters of propylene glycol are esterified with the medium chain fatty acids or fatty acid anhydrides to obtain the desired ML/LM diesters. When fatty acids are used as the reactant, an at least stoichiometric amount of medium chain fatty acids is used relative to the monoesters, i.e. a mole ratio of fatty acid to monoester of at least about 1:1. Typically, the mole ratio of fatty acid to monoester is in the range of from about 1.5:1 to about 12:1, with a preferred mole ratio in the range of from about 3:1 to about 9:1, i.e. an excess of medium chain fatty acids is preferred. Mole ratios higher than about 12:1 can be used in this process, but are usually not desirable since this results in a significant amount of unreacted fatty acid that needs to be removed during subsequent purification and does not significantly increase the level of desired ML/LM diesters.

When fatty acid anhydrides are used as the reactant, the medium chain fatty acid anhydrides can be used in a stochiometric amount relative to the monoester, i.e. a mole ratio of fatty acid anhydride to monoester of at least about 1:1. Typically, the mole ratio of fatty acid anhydride to monoester is in the range of from about 1:1 to about 2:1, with a preferred mole ratio in the range of from about 1:1 to about 1.5:1. Mole ratios higher than about 2:1 can be used but do not significantly increase the level of desired ML/LM diesters.

An important aspect of the preferred process of the present invention is that it is typically carried out in a solvent-free system. At the temperatures at which the esterification process is carried out, the mixture of propylene glycol monoesters and medium chain fatty acids/fatty acid anhydrides forms an essentially homogeneous melt. Accordingly, solvents are not required in carrying out the preferred process of the present invention.

Another important aspect of the preferred process of the present invention is that it can be carried out in the substantial absence of an esterification catalyst. As used herein, the term "substantial absence of an esterification catalyst" means that the preferred process of the present invention is carried out without intentionally adding such catalysts. Esterification catalysts such as strong bases (e.g., sodium hydroxide, sodium methoxide, pyridine or alkyl substituted pyridine derivatives such as N,N-dimethyl 1,4-aminopyridine) and strong acids (e.g., phosphoric acid, cationic ion exchange resins such as Amberlite IR120 (H+), p-toluenesulfonic acid, sulfuric acid or perchloric acid) are not typically required in order to carry out the preferred process of the present invention. However, in certain instances, e.g., medium chain fatty acids are not in excess, strong base or strong acid esterification catalysts can be used in the preferred process of the present invention to increase the esterification rate. Besides strong base or strong acid esterification catalysis, enzymatic catalysts such as lipase can also be used in the preferred process of the present invention with appropriate adjustment of reaction conditions.

Another important aspect of the preferred process of the present invention is the esterification temperatures used. The esterification of propylene glycol monoesters with medium chain fatty acids can be carried out at a temperature in the range of from about 175° to about 250° C., and preferably in the range of from about 175° to about 225° C. The esterification of propylene glycol monoesters with medium chain fatty acid anhydrides can be carried out at lower temperatures in the range of from about 100° to about 190° C., and preferably in the range of from about 120° to about 160° C.

The esterification of propylene glycol monoesters with medium chain fatty acid anhydrides according to the preferred process of the present invention is preferably carried out in a substantially anhydrous system to avoid converting the anhydrides to the respective fatty acids. The esterification of propylene glycol monoesters with medium chain fatty acids according to the preferred process of the present invention requires water that is generated during the reaction be continuously removed from the reaction mixture. It has been found that water generated during this reaction that remains in the reaction mixture can cause hydrolysis of the resulting esters, and therefore lead to undesired rearrangement that decreases the level of desired ML/LM diesters. Suitable methods for continuous removal of this generated water include vacuum stripping of the reaction mixture (e.g., at pressures of from 50 to 300 mm Hg), inert gas (e.g., nitrogen) sparging of the reaction mixture using high shear mixing with high gas velocities, adsorption by hydrophilic materials such as zeolite molecular sieves, activated carbon and activated alumina, or combinations of these techniques. For example, in the case of nitrogen gas sparging, 0.1 to 10 l./min. gas flow per liter of reaction mixture in conjunction with high shear mixing (e.g. a 5 to 600 m./min. tip speed) are preferred for removal of generated water. (This degree of high shear mixing is typically achieved by a drive motor energy input of 1.5 to 3 kilowatts per 1000 liters of reaction mixture.) In addition, it is preferred that the fatty acids and monoester starting materials be essentially anhydrous (e.g. by vacuum dehydration) prior to esterification.

The preferred process of the present invention can be carried out as either a batch or continuous reaction system. For example, plug or mixed flow configurations can be used to continuously react the medium chain fatty acids or fatty acid anhydrides with the propylene glycol monoesters in one or more stages. Alternatively, thin film-type reaction or spray esterification systems operated at higher temperatures with short residence times can be used in this esterification step. Typically, the solid or liquid propylene glycol monoester are added to the melted medium chain fatty acids or fatty acid anhydrides at the desired esterification temperature to minimize disproportionation of the monoesters to diester/propylene glycol. The propylene glycol monoesters are also typically added slowly to the melted fatty acids or fatty acid anhydrides at a controlled rate of addition during the esterification to minimize the concentration of unreacted monoesters in the mixture (e.g., to about 0.2% or less), and thus minimize the formation of LL diesters. When medium chain fatty acid anhydrides are used, the reactants, in particular the propylene glycol monoesters, are also preferably dry (substantially anhydrous) to avoid converting the anhydrides to the respective fatty acids. The esterification is also preferably carried out under an inert gas atmosphere (e.g., nitrogen) to prevent moisture pickup and to maintain good color in the resulting esterified products.

The particular reaction times for carrying out this preferred process can vary greatly depending upon whether medium chain fatty acids or fatty acid anhydrides are used, the mole ratio of fatty acids/anhydrides to propylene glycol monoesters used, the particular esterification temperatures used, the type of catalyst used (if any), and the yield/degree of purity desired for the ML/LM diesters. Usually, reaction times of from about 2 to about 12 hours are suitable for agitated (e.g., stirred) batch reaction systems using medium chain fatty acids as the reactant. When medium chain fatty acid anhydrides are used, reaction times of from about 1 to about 3 hours are suitable for batch reaction systems. Preferably, the esterification with medium chain fatty acids is carried out for a period of from about 2 to about 3 hours, while the esterification with medium chain fatty acid anhydrides is carried out for a period of from about 1 to about 2 hours to agitated batch reaction systems. (Equivalent residence times can be used in continuous reaction systems.) The esterification reaction is typically allowed to proceed until there has been an at least about 99% conversion of the propylene glycol monoesters to the respective diesters.

After the esterification of propylene glycol monoesters with medium chain fatty acids or fatty acid anhydrides has been carried out for the appropriate time, the level of desired ML/LM diesters in the reaction mixture is usually at least about 75%. When medium chain fatty acids are used as the reactant, the level of desired ML/LM diester is typically at least about 90% and more typically at least about 95%, when using preferred esterification conditions and high purity fatty acid and propylene glycol monoester reactants. When medium chain fatty acid anhydrides are used as the reactant, the level of the desired ML/LM diesters is typically at least about 95% and more typically at least about 98%, when using preferred esterification conditions and high purity fatty acid anhydride and propylene glycol monoester reactants.

The particular level of ML/LM diesters present in the mixture will depend upon a number of factors, including whether medium chain fatty acids or fatty acid anhydrides are used as the reactant, the purity of the fatty acid/fatty acid anhydride and propylene glycol monoester reactants, and the reaction conditions used. For example, the esterification of an at least 99.5% pure mixture of propylene glycol mmonobehenate/monoarachidate (56%/36%) with an at least 98% pure mixture of caprylic ($C_8$) fatty acid in a mole ratio of fatty acid to monoesters of 9:1 at a reaction temperature of 200° C. for 3 hours results in a reaction mixture containing a level of 96.3% ML/LM propylene glycol diesters ("ML/LM"=carbon numbers $C_{22}$ to $C_{34}$). In the case of the esterification of an at least 99.5% pure mixture of propylene glycol monobehenate/monoarachidate (56%/36%) with an at least 99% pure caprylic ($C_8$) fatty acid anhydride in a mole ratio of fatty acid anhydride to monoesters of 1.2:1 at a reaction temperature of 140° C. for 1.75 hours typically results in a reaction mixture containing a level of 98.7% ML/LM propylene glycol diesters.

The level of ML/LM diesters in this reaction mixture can be sufficiently high so that further purification is unnecessary, particularly depending upon the proposed use of the ML/LM diesters. However, purification of the reaction mixture resulting from the esterification step is typically required in order to remove various components such as unreacted medium chain fatty acids and fatty acid anhydrides and by-products such as MM and LL diesters.

Subsequent purification can be carried out by a variety of techniques, or combinations of techniques. Residual fatty acid anhydrides can be converted to the respective fatty acids by the addition of water and then heating at 100° C. for 15 to 30 minutes. Alternatively, the anhydrides can be removed along with any residual medium chain fatty acids. Residual medium chain fatty acids can be removed by precipitation as salts (e.g., by addition of a base such as potassium carbonate). Both the fatty acids and anhydrides can be removed by the use of reverse osmosis membranes (e.g., NIRO HR98 polyamid/polysulfone thin film composite membranes having a 200-400 molecular weight cutoff), by flash evaporation, by steam stripping, or by vacuum distillation to decrease the combined level of fatty acids/anhydrides in the reaction mixture to about 5% or less. MM diesters, and any residual fatty acids/anhydrides, can be removed by, for example, flash evaporation, molecular distillation using a wiped film evaporator (e.g., at temperatures of 175° to 200° C. and at pressures of 0.001 to 0.2 mm. Hg, preferably with the fatty acids/anhydrides/MM diesters as the distillate fraction), or by fractional crystallization using ethanol, acetone or hexane as the solvent, to decrease the level of MM diesters in the reaction mixture to about 1% or less, and the level of residual fatty acids/anhydrides to about 0.1% or less. The LL diesters can be separated from the ML/LM diesters by, for example, molecular distillation (e.g., at 200° to 225° C. and 0.001 to 0.01 mm Hg pressure, preferably with the desired ML/LM diesters as the distillate fraction), winterization (e.g., at 50° C. to promote crystal growth, followed by 30° to 40° C. filtration), or solvent fractional crystallization using ethanol, acetone or hexane as the solvent, to decrease the level of LL diesters in the reaction mixture to about 1% or less. Preferably, the reaction mixture is molecularly distilled to minimize color and the levels of unsaponifiables. Surprisingly, the flavor of the distillate is very bland, free of off-flavors and very low in by-products (e.g., hydrocarbons, di-fatty ketones, etc.) when properly molecularly distilled using short residence times and high vacuums.

Any fatty acids, fatty acid anhydrides, MM diesters or LL diesters removed during purification can be recycled to provide sources of medium chain fatty acids or fatty acid anhydrides or long chain fatty acid monoesters of propylene glycol for further esterification according to the preferred process of the present invention. Alternatively, these materials can be reincorporated into the esterification mixture at low levels for subsequent reaction to provide additional ML/LM diesters.

The purified mixture of ML/LM diesters can also be subjected to bleaching and deodorizing steps for color and flavor/aroma improvement using conventional techniques well known in the fats and oils art. During batch deodorization, it is important to maintain the temperature below 250° C. and to use high steam sparge rates under a good vacuum to minimize rearrangement. Alternatively, the reaction mixture can be bleached using conventional bleaching earths and/or activated carbon prior to purification.

E. Use of Preferred Propylene Glycol Diester Compositions as Reduced Calorie Cocoa Butter Substitutes and Hard Butters The preferred propylene glycol diester compositions of the present invention are especially useful as reduced calorie cocoa butter substitutes and hard butters in flavored reduced calorie confectionery products, particularly chocolate-flavored confectionery products. These flavored confectionery products comprise:
(a) a flavor-enhancing amount of a flavor component;
(b) from about 25 to about 45% of a fat component comprising:
  (1) at least about 60% of the preferred propylene glycol diester compositions according to the present invention;

(2) up to about 25% milkfat;
(3) up to about 15% cocoa butter;
(4) optionally other fat-soluble confectionery ingredients such as other compatible confectionery fats or reduced calorie fat substitutes, crystallization promoters, bloom inhibitors and/or emulsifiers; and
(c) from about 55 to about 75% other nonfat confectionery ingredients such as sugar, sugar alcohols, reduced calorie sweeteners, reduced calorie bulking agents and nonfat milk solids.

1. Flavor Component

The flavor component comprises flavor constituents which impart positive flavor characteristics, and optionally non-flavor constituents normally present in flavor compositions, e.g. flavor carriers. As used herein, the term "flavor-enhancing amount" refers to an amount of the flavor component sufficient to impart positive flavor characteristics to the confectionery product. As such, the amount of the flavor component sufficient to be "flavor enhancing" can depend on the flavor source used, the flavor effects desired and like factors. Typically, the flavor component (nonfat constituents) comprises from about 0.1 to about 25% of the confectionery product.

A variety of flavor sources can be used to form the flavor component. A particularly preferred flavor source is a chocolate flavor. Suitable chocolate flavors can be derived from chocolate-liquor, cocoa powder, or blends thereof. As used herein, "chocolate-liquor" refers to the solid or semi-plastic food prepared by finely grinding cacao nibs. Chocolate-liquor usually contains from about 50 to about 58% cocoa butter fat. As used herein, "cocoa powder" refers to the residual material remaining after part of the cocoa butter fat has been removed from ground cacao nibs. Cocoa powder usually contains from about 10 to about 22% cocoa butter fat. Other sources of flavor include vanillin, ethyl vanillin, spices, coffee, brown sugar, synthetic flavors, etc., as well as mixtures of these flavors.

2. Fat Component

As used herein, the term "fat component" refers to the propylene glycol diesters of the present invention, all glycerides (i.e. triglycerides, diglycerides and monoglycerides), as well as all nonglyceride reduced calorie fat substitutes, crystallization promoters, bloom inhibitors and emulsifiers, present in the confectionery product. For example, if chocolate-liquor is used to formulate chocolate-flavored products, the cocoa butter portion is included as part of the fat component. If milk solids are used, for example, in milk chocolate-flavored compositions, any milkfat present is included as part of the fat component.

The fat component comprises from about 25 to about 45% of the confectionery product. The particular amount of the fat component which is suitable depends on the particular application in which the flavored confectionery product is used. For molding applications (e.g., chocolate-flavored bars), the fat component preferably comprises from about 28 to about 32% of the confectionery product. For enrobing applications (e.g., enrobed candy bars or cookies), the fat component preferably comprises from about 30 to about 45% of the confectionery product. For depositing applications (e.g. chocolate-flavored chips), the fat component preferably comprises from about 25 to about 30% of the confectionery product.

The major constituent in this fat component is the preferred reduced calorie propylene glycol diester compositions of the present invention. The particular amount of these preferred propylene glycol diesters that are present in the fat component depends upon the degree of calorie reduction desired for the flavored confectionery product. These propylene glycol diester compositions comprise at least about 60% of the fat component. Preferably, these preferred propylene glycol diester compositions comprise at least about 75% of the fat component, more preferably at least about 80%, and most preferably at least about 85% of the fat component.

The fat component can tolerate up to certain levels of milkfat and cocoa butter. Milkfat (sometimes referred to as "butterfat") is usually present in the fat component as the result of the inclusion of milk solids in milk chocolate-flavored confectionery products. However, milkfat can also be present as the result of the inclusion of butter oil. Milkfat can generally be tolerated in the fat component at levels up to about 25%. For milk chocolate-flavored products, as well as pastel coatings (e.g., mint-flavored confectionery coating products) that optionally contain cocoa butter, milkfat is typically present in the fat component at a level of from about 3 to about 15%, and preferably at a level of from about 5 to about 10%.

The cocoa butter present in the fat component can be included as an added fat. However, cocoa butter is more typically included as a result of its being present in the source of chocolate flavoring (e.g., cocoa powder, chocolate liquor, or blends thereof) used in the flavored confectionery products. Cocoa butter can generally be tolerated in the fat component at levels up to about 15%. For chocolate-flavored confectionery products, cocoa butter is typically present in the fat component at a level of from about 1 to about 15%, and more preferably at a level of from about 5 to about 10%.

The fat component can also comprise other compatible confectionery fats, i.e. partial or total cocoa butter replacers, as well as cocoa butter equivalents. These compatible confectionery fats include cocoa butter substitutes derived from illipe butter (Borneo tallow), Shea butter, Mowrah fat and palm oil. Suitable cocoa butter substitutes derives from palm oil are the POP fats disclosed in U.S. Pat. No. 4,594,259 to Baker et al, issued Jun. 10, 1986, which is incorporated by reference. These cocoa butter substitute fats can be included as partial or total replacements for the cocoa butter present in the fat component. However, because of their higher caloric value, these cocoa butter substitute fats are typically not included in the fat component.

If desired, other compatible reduced calorie fat substitutes, such as sucrose polyesters of $C_{10}$–$C_{18}$ saturated fatty acids having melting properties similar to cocoa butter, can be included in the ft component. See U.S. Pat. No. 4,810,516 to Kong-Chan, issued Mar. 7, 1989 and U.S. Pat. No. 4,822,875 to McCoy et al, issued Apr. 18, 1989, which are incorporated by reference.

If desired, the fat component can include crystallization promoters and bloom inhibitors. Suitable crystallization promoters include tribehenin, palm oil stearine, completely hydrogenated or substantially completely hydrogenated high erucic acid rapeseed oil (i.e. I.V. of about 2 or less), sodium dipalmitate, diacetyl tartaric acid monoglycerides, and 2-oleic-1,3-dibehenin. Suitable bloom inhibitors include sorbitan tristearate, sorbitan monostearate, sucrose mono- and diesters, lactylated mono- and diglycerides, ethoxylated sorbitan monostearate (e.g., polysorbate 60), ethyoxylated sorbitan tristearate (e.g., polysorbate 65), and polyglycerol esters such as those disclosed in U.S. Pat. No. 4,847,105 to Yokobor et al, issued Jul. 11, 1989, which is incorporated by reference. Sorbitan monostearate and sorbitan tristearate are particularly preferred as bloom inhibitors, especially since these materials also alter (i.e. soften) the mouthfeel of the resulting chocolate-flavored product. These crystallization promoters and bloom inhibitors are included in an effective amount, typically in the range of from about 0.5 to about 8% of the fat component.

Flavored confectionery products usually include an emulsifier to "wet" the sugar particles with the fat component. Suitable emulsifiers include sorbitan monostearate, ethoxylated sorbitan monostearate (e.g., polysorbate 60), polyglycerol esters, sucrose partial esters, and particularly lecithin (natural or synthetic). (Some of these emulsifiers, such as sorbitan monostearate, polysorbate 60 and polyglycerol esters, also function as bloom inhibitors.) These emulsifiers can be present at up to about 1% of the confectionery product, and typically at up to about 0.5%. Preferred levels of emulsifier are from about 0.05 to about 0.5% of the confectionery product.

3. Other Nonfat Confectionery Ingredients

One particularly important nonfat ingredient in these flavored confectionery products is sugar. Sugar is typically present in such products at from about 35 to about 60%, and preferably at from about 40 to about 55%, of the product. Especially for chocolate-flavored confectionery products, the source of sugar needs to be essentially dry. Sources of sugar include sucrose, fructose, glucose, maltose and mixtures thereof. The sugar typically has a particle size in the range of from about 0.0002 to about 0.0016 inches (from about 5 to about 40 microns) in the finished chocolate-flavored product.

For dietary or cariogenic reasons, the sugar can be completely or partially substituted with a sugar alcohol. Suitable sugar alcohols include sorbitol, xylitol, mannitol, maltitol, lactitol, and mixtures thereof. For further calorie reduction, the sugar or sugar alcohol can be completely or partially substituted with an effective amount of a reduced calorie sweetener. These reduced calorie sweeteners include, but are not limited to, aspartame, saccharin, alitame, thaumatin, dihydrochalcones, cyclamates, steviosides, glycyrrhizins, synthetic alkoxy aromatics, such as Dulcin and P-400, sucralose, suosan, miraculin, monellin, talin, cyclohexysulfamates, substituted imidazolines, synthetic sulfamic acids such as acesulfame, acesulfam-K and n-substituted sulfamic acids, oximes such as perilartine, rebaudioside-A, peptides such as aspartyl malonate and succanilic acids, dipeptides, amino acid based sweeteners such as gem-diaminoalkanes, meta-aminobenzoic acid, L-aminodicarboxylic acid alkanes, and amides of certain alipha-aminodicarboxylic acids and gem-diamines, and 3-hydroxy-4-alkyloxyphenyl aliphatic carboxylates or heterocyclic aromatic carboxylates.

When sugar is replaced, especially with the above reduced calorie sweeteners, it can be desirable to include reduced calorie bulking agents, e.g., at from about 20 to about 60% of the confectionery product. Suitable bulking agents include poorly digested carbohydrates, for example, polydextrose, and cellulose or cellulose derivatives, such as carboxymethylcellulose, carboxyethylcellulose, hydroxypropylcellulose, methylcellulose and microcrystalline cellulose. Other suitable bulking agents include neosugar, arabinogalactan, beta-glucanhydrolysate, hydrogenated starch hydrolysate, dextrins, maltodextrins, mannitol, isomalt, lactitol, and dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus, pulp and vesicle solids, apples, apricots, watermelon rinds, and seeds (e.g., psyllium).

A particularly desirable class of poorly digested bulking agents are certain 5-C-hydroxymethylhexose compounds and their derivatives that act like "reduced calorie sugars" in terms of their ability to provide the functional properties of nutritive carbohydrate sweeteners (e.g., sucrose), but without the sweetness of the calories. See European patent application 341,062 to Mazur, published Nov. 8, 1989 (herein incorporated by reference), which discloses these reduced calorie sugars and their synthesis and European patent application 341,063 to Mazur et al, published Nov. 8, 1989 (herein incorporated by reference), for an alternative synthesis of the 5-C-hydroxymethylaldohexoses. Preferred reduced calorie sugars include:

5-C-hydroxymethyl-L-arabino-hexopyranose;
5-C-hydroxymethyl-D-xylo-hexopyranose;
1,6-anhydro-5-C-hydroxymethyl-$\beta$-L-altopyranose;
1,6-anhydro-5-C-hydroxymethyl-$\beta$-L-idopyranose;
1,6-anhydro-5-C-hydroxymethyl-$\beta$-L-gulopyranose;
methyl 5-C-hydroxymethyl-D-xylo-hexopyranoside;
methyl 5-C-hydroxymethyl-L-arabino-hexopyranoside;
ethyl 5-C-hydroxymethyl-L--arabino-hexopyranoside;
5-C-hydroxymethyl-L-arabino-hexopyranosyl glycerol;
5-C-hydroxymethyl-$\alpha$-D-glucopyranosyl-$\beta$-D-fructo furanoside;
5-C-hydroxymethyl-$\alpha$-D-galactopyranosyl-(1$\rightarrow$4)-D-galactopyranose;
5-C-hydroxymethyl-$\beta$-D-galactopyranosyl-(1$\rightarrow$6)-D-galactopyranose;
5-C-hydroxymethyl-$\beta$-L-arabino-hexopyranosyl-$\alpha$-D-glucosyl-$\beta$-D-fructose;
5-C-hydroxymethyl-D-galactopyranosyl-D-glucitol;
5-C-hydroxymethyl-$\alpha$-L-arabino-hexopyranosyl-D-sorbitol;
arabinogalactan derivatives wherein at least one galactosyl group is converted to a 5-C-hydroxymethyl group;
and mixtures thereof.

Especially in milk chocolate-flavored products and pastel coatings, the flavored confectionery product can also include milk solids (essentially dry), usually at from about 9 to about 20% of the product, and typically at from about 12 to about 18%. Suitable sources of essentially dry milk solids can be obtained from cream, milk, concentrated milk, sweetened condensed milk, skim milk, sweetened condensed skim milk, concentrated buttermilk, and the like. (As previously stated, any fat present in the milk solids, such as milkfat, is considered part of the fat component.)

Other minor ingredients, such as salt, normally present in fat-based confections can be included, as well as optional components, such as the pharmaceutical actives disclosed at column 7, lines 1-35 of U.S. Pat. No. 4,786,502 to Chapura et al, issued Nov. 22, 1988, which is incorporated by reference.

4. Preparation of Flavored Confectionery Products, in Particular Chocolate-Flavored Products The flavored confectionery products of the present invention can be prepared by basically using standard techniques for making cocoa butter-based chocolate products. The following discussion will generally be with regard to the preparation of chocolate-flavored products, which are highly preferred flavored confectionery products according to the present invention. However, the preparation of non-chocolate-flavored confectionery products (e.g., pastel coatings) can be achieved by using the same or similar steps.

Initially, a chocolate-flavored mixture of confectionery ingredients is formed. Some typical chocolate formulations include milk chocolate-flavored formulations, and dark chocolate-flavored formulations. In addition to the reduced calorie propylene glycol diesters, milk chocolate-flavored formulations typically comprise sugar, cocoa powder, optionally chocolate liquor, milk solids, lecithin as the emulsifier, and other confectionery ingredients such as salt. Dark chocolate-flavored formulations are similar to milk chocolate-flavored compositions but typically do not include milk solids.

The total fat present in these chocolate-flavored formulations can be adjusted to provide the desired viscosity. For molding or depositing applications, the amount of total fat is preferably lower. For enrobing applications, the amount of total fat is preferably higher. The ratios of sugar, cocoa powder, chocolate liquor, and milk solids can vary depending upon the flavor desired.

The chocolate-flavored formulations are prepared by mixing the ingredients to "wet" them with the reduced calorie propylene glycol diesters and to provide a consistency suitable for the subsequent refining step. During this mixing step, sugar, milk solids, salt, and cocoa powder are added to a mixer. Then, the melted chocolate-liquor (if any), a portion of the reduced calorie propylene glycol diesters and optionally a portion of the total lecithin are added to the mixer. These ingredients are stirred for a period of time sufficient to "wet" the dry ingredients with the fat, including the propylene glycol diesters. The particular time period is not critical and is typically about 15 minutes. During this mixing step, the contents of the mixer are heated to a temperature of at least about 100° F. (37.8° C.). Contact with moisture is avoided during this step. The consistency of the chocolate formulation after mixing is typically that of soft putty.

After mixing, the chocolate-flavored formulation is refined to reduce the solids, in particular the sugar, to the desired particle size, typically in the range of from about 0.0002 to about 0.0016 inches (from about 5 to about 40 microns). This refining step also coats the solids with the fat. Typically, four or five water-cooled rolls, each progressively faster in speed, are used to refine the formulation. Pressure between the rolls is adjusted to achieve the desired fineness for the solids. As in the dry mixing step, contact with moisture is avoided during refining. In particular, the rolls are not cooled to or below the dewpoint of ambient air. The consistency of the chocolate-flavored formulation after refining is typically that of flakes.

After refining, the chocolate-flavored formulation is dry-conched to remelt and redistribute the fat to the surface of the solids in the refined mix. The moisture content of the mix is reduced to about 1% or less. Certain volatile compounds are also removed which improves the flavor. In this dry conching step, flakes from the refining step are first broken into a powdery mass in a mixer which is typically heated to at least about 100° F. (37.8° C.). When this temperature is reached, the mass has the consistency of lumps of firm putty. The contents of the mixer can be adjusted to temperatures in the range of from about 100° to about 160° F. (from about 37.8° to about 71.1° C.) for milk chocolate-flavored formulations and to temperatures in the range of from about 120° to about 180° F. (from about 48.9° to about 82.2° C.) for dark chocolate-flavored formulations. The total time required for this dry-conching step can typically range from about 1 to about 72 hours.

After dry-conching, the chocolate-flavored formulation is wet-conched. During wet-conching, a portion of the reduced calorie propylene glycol diesters and optionally lecithin are added and then mixed to provide a viscous fluid mass. The contents of the mixer can be adjusted to temperatures in the range of from about 110° to about 180° F. (from about 43.3° to about 82.2° C.), the particular temperature depending upon the particular chocolate-flavored formulation. The total time required for this wet-conching step can typically range from about 5 to about 20 hours. After this wet-conching step, the remaining reduced calorie propylene glycol diesters and lecithin are added to adjust the viscosity of the mass to that required for the intended application. Mixing is continued, typically for about 10 to about 60 minutes. The temperature is also typically reduced to the range of from about 100° to about 110° F. (from about 37.8° to about 43.3° C.) to provide a fluid or liquid chocolate-flavored mass.

The fluid/liquid chocolate-flavored mass is then ready for molding, depositing or enrobing applications. Molding and depositing applications include the formulation of chocolate-flavored bars and chocolate chips, while enrobing applications include candy bars, ice cream bars and cookies covered with a chocolate-flavored coating. In molding or depositing applications, the fluid/liquid chocolate-flavored mass is simply poured into the appropriate mold or deposited onto a flat surface such as a moving belt. In enrobing applications, the fluid/liquid chocolate-flavored mass is applied to the appropriate substrate such as a confectionery nougat center, ice cream center or cookie center using conventional enrobing equipment.

The molded, deposited or enrobed chocolate-flavored product is typically subjected to a partial precrystallization step in order to insure that the product sets up in a stable form resistant to bloom formation, especially if the product is subjected to thermal stress. In one embodiment of this crystallization step, the fluid/liquid chocolate-flavored mass is quickly cooled to a temperature of about 40° F. (4.4° C.) or less. As used herein, "quickly cooled" refers to a temperature decrease at a rate sufficient to induce nucleation of the reduced calorie propylene glycol diesters present in the chocolate-flavored confectionery mass and to form numerous $\beta'$ seed crystals that are very small in size. For example, cooling the chocolate-flavored confectionery mass from a temperature of from about 100° to about 110° F. (from about 37.8° to about 43.3° C.) to a temperature of about 40° F. (4.4° C.) or less over a period of from about 3 to about 5 minutes has been found to be sufficient to induce nucleation of these reduced calorie propylene glycol diesters and to form numerous $\beta'$ seed crystals that are very small in size. This rapid cooling can be carried out in a refrigerated cooling tunnel or in a blast freezer using a suitable inert coolant such as liquid carbon dioxide.

Once the chocolate-flavored product has been cooled to the appropriate temperature, it is sufficiently firm to be wrapped or otherwise packaged. It is desirable to control the ambient humidity so as to avoid moisture condensation on the cooled product surface; such condensation can cause visible sugar crystals to form on the product surface. This cooled product is held at a temperature (or at various temperatures) of about 55° F. (12.8° C.) or less, preferably about 40° F. (4.4° C.) or less, for a period of at least about 5 minutes, preferably for a period of at least about 10 minutes, and then warmed to a temperature of about 70° F. (21.1° C.) or higher. Once the $\beta'$ seed crystals have been formed, the remaining portion of the reduced calorie propylene glycol diesters in the chocolate-flavored product "spontaneously" crystallize into a solid, stable $\beta'$ phase, even when warmed directly to a temperature of about 70° F. (21.1° C.) or higher. However, it has been found that holding the product as cooler temperatures (e.g., about 40° F. (4.4° C.) or less) for a sufficient period (e.g., at least about 10 minutes) insures that the resulting chocolate-flavored product has a smooth, homogeneous appearance that is resistant to bloom formation, even when subjected to thermal stress. This is believed to be due to the fact that the remaining portion of the reduced calorie propylene glycol diesters transforms into a stable $\beta'$ phase composed of relatively small fat crystals.

Chocolate-flavored products resistant to bloom formation can also be obtained by an alternative crystallization sequence that is analogous to the tempering of cocoa butter-based chocolate products. In this alternative crystallization sequence, the fluid/liquid chocolate-flavored mass is cooled to a temperature of from about 78° to about 83° F. (from about 25.6° to about 28.3° C.) prior to molding, depositing or enrobing, and then held at this temperature for a period of at least about 10 minutes, and typically for a period of from about 15 minutes (for temperatures closer to 78° F. (24.6° C.)) to about 45 minutes (for temperatures closer to 83° F. (28.3° C.)). This is believed to induce a portion of the reduced calorie propylene glycol diesters present in the chocolate-flavored mass to form numerous $\beta'$ seed crystals of very small size. After this initial cooling and holding, the chocolate-flavored mass is then heated to a temperature of from about 84° to about 95° F. (from about 28.8° to about 35° C.) to melt some, but not all, of the $\beta'$ propylene glycol diester seed crystals, and thus reduce the viscosity of the chocolate-flavored mass. (Reducing the viscosity of the chocolate-flavored mass is particularly important for enrobing applications. If viscosity reduction is not required, heating of the chocolate-flavored mass can be omitted.) Once the chocolate-flavored mass has been heated, it is then ready for molding, depositing or enrobing. (Optionally, this alternative crystallization sequence can be repeated one or more times prior to molding, depositing or enrobing.) The molded, deposited or enrobed chocolate-flavored product is cooled to a temperature of about 50° F. (10° C.) or less, preferably about 40° F. (4.4° C.) or less, for a period of at least about 10 minutes, preferably at least about 15 minutes, and then warmed to a temperature of about 70° F. (21.1° C.) or higher to provide a fully crystallized chocolate-flavored products. During these cooling and warming steps it is believed that the remaining portion of the reduced calorie propylene glycol diesters is transformed into a stable $\beta'$ phase composed of relatively small fat crystals.

The crystallization of the chocolate-flavored mass can be carried out in various types of conventional chocolate tempering equipment, e.g., a Solich turbo-temperer, a scraped wall heat exchanger, etc. For example, the fluid uncrystallized chocolate-flavored mass can be passed through a scraped wall heat exchanger having an inside wall temperature maintained at from about $-10°$ F. to about 35° F. (from about $-23.3°$ to about 1.7° C.) to induce nucleation of the reduced calorie propylene glycol diesters. The exiting nucleated mass having a bulk temperature of about 70° F. (21.1° C.) or higher is then agitated with gentle shear in order to disperse the $\beta'$ seed crystals before heating to reduce the viscosity of the mass prior to molding, depositing or enrobing applications.

The crystallization methods previously described generate $\beta'$ seed crystals in situ from the reduced calorie propylene glycol diesters. If desired, a portion of the fully crystallized chocolate-flavored products formed by these methods can be ground up and then added in minor amounts (e.g., from about 5 to about 10% of the total formulation) to the uncrystallized fluid/liquid chocolate-flavored mass. This seeded chocolate-flavored mass is then heated to a temperature of from about 84° to about 95° F. (from about 28.8° C. to about 35° C.) to control its viscosity prior to molding, depositing or enrobing. The molded, deposited or enrobed chocolate-flavored product is then cooled to a temperature of about 50° F. (10° C.) or less, preferably at least about 40° F. (4.4° C.) or less, for a period of at least about 10 minutes, preferably at least about 15 minutes, to provide a fully crystallized chocolate-flavored product.

These fully crystallized chocolate-flavored products exhibit excellent thermal stability against bloom formation. Surprisingly, these fully crystallized products exhibit excellent gloss that is maintained even when subjected to thermal stress (e.g., 1 hour at 90° F., 32.2° C.) followed by ambient (e.g. 70° F., 21.1° C.) storage.

G. Analytical Methods

1. Carbon Number Profile (CNP)

The carbon number profile (CNP) of the propylene glycol diesters is determined by programmed temperature-gas chromatography using a short fused silica column coated with methyl silicone for analysis and characterization of the composition by molecular weight. See D'Alonzo et al, "Analysis of Processed Soy Oil by Gas Chromatography," *J. Am. Oil Chem. Soc.*, Vol. 58 (1981), pp. 214 et seq., and Geeraert et al, "Capillary GC of Triglycerides in Fats and Oils Using a High Temperature Phynylmethyl Silicone Stationary Phase. Part II. The analysis of Chocolate Fats", *J. Am. Oil Chem. Soc.*, Vol. 64 (1987), pp. 100 et seq., for the general CNP methodology. The diesters are separated according to their respective carbon numbers, wherein the carbon number defines the total number of carbon atoms on the combined fatty acid residues. The carbon atoms on the propylene glycol molecule are not counted. Diesters with the same carbon number will elute as the same peak. For example, a diester composed of one $C_8$ (caprylic) and one $C_{22}$ (behenic) fatty acid residue will co-elute with diesters composed of one $C_{10}$ (capric) and one $C_{20}$ (arachidic) fatty acid residue.

In practice, the diester samples are dissolved in chloroform and derivatized with a silylating agent to obtain good chromatographic separation. Results are reported as normalized area percents of each diester from carbon numbers 16 through 48. A reference standard is used to assure proper performance of the analysis.

Preparation of the diester sample for analysis is as follows: The diester sample is heated at 80° C. until completely melted. A 500 microl. portion of the melted sample is pipetted into a 5 ml. volumetric flask, and is then diluted to volume using chloroform. A 250 microl. portion of the solution in the flask is transferred to an autosampler vial and then 1.0 ml of bis (trimethylsilyltrifluoroacetamide) (BSTFA) is pipetted into the vial which is then capped. The contents in the vial are heated for 5 minutes at 100° C. and then cooled before analysis.

For determining the CNP of the prepared diester samples, a Hewlett-Packard 5890 series gas chromatograph equipped with temperature programming and a hydrogen flame ionization detector is used together with an integrating recorder. A 2 m. long, 0.25 mm. diameter fused silica capillary column coated with a thin layer of methyl silicone (J&W DB-1) is used with a glass insert packed with silated glass wool (HP 18740-80190) and a high temperature graphite O-ring. The column oven temperature is controlled according to a specified pattern by the temperature programmer. The hydrogen flame ionization detector is attached to the outlet port of the column with the signal generated by the detector being amplified by an electrometer into a working input signal for the integration system which prints out the gas chromatograph curve and electronically integrates the area under the curve. The following instrument conditions are used with the gas chromatograph:

| | |
|---|---|
| Septum purge | 2-3 ml./min. |
| Split vent flow | 380 ml./min. |
| Split ratio | 85/1-100/1 |
| Hydrogen carrier gas | 4 ml./min. |
| Hydrogen pressure | 40 psi |
| Nitrogen make-up gas | 25 ml./min. |
| Detector temperature | 375° C. |
| Detector hydrogen flow | 30 ml./min |
| Detector air flow | 330 ml./min. |
| Detector make-up | 25 ml./min. |

1.0 microl. of the prepared diester sample is injected by a gas-tight syringe, or a HP 7673A microdrop injector with tray thermostated to 25° C., into the sample port of the chromatograph. The components in the sample port are warmed up to a temperature of 340° C. and swept by the hydrogen carrier gas to push the components into the column. The column temperature is initially set at 80° C. and held at this temperature for 0.5 min. The column is then heated up to a final temperature of 340° C. at a rate of 15° C./min. The column is maintained at the final temperature of 340° C. for an additional 10 minutes.

The chromatographic peaks generated are then identified based on the retention times of the peak areas measured. Peak identification is accomplished by comparison to known pure glycerides and diesters previously analyzed. The peak area is used to calculate the percentage of diesters having a particular Carbon Number ($C_N$) according to the following equation:

$$\% \, C_N = (\text{Area of } C_N/S) \times 100$$

wherein S=sum of Area of $C_N$ for all peaks generated.

The sums of the diester groups (i.e. MM, ML/LM, and LL) are calculated from the sums of the peak areas of the respective diesters as follows: "MM"=diesters having carbon numbers $C_{16}$ through $C_{20}$; "ML/LM"=diesters having carbon numbers $C_{22}$ through $C_{34}$; and "LL"=diesters having carbon numbers $C_{36}$ through $C_{48}$. The group sums are normalized and reported on a fatty acid-free basis.

A reference standard is used to verify proper performance of the CNP procedure. This standard is prepared from individual fatty acid or triglyceride standards (Nu-Chek Prep) and has the following composition:

| Component | % |
|---|---|
| Behenic acid | 0.68 |
| Trioctanon | 0.70 |
| Tridecanon | 7.20 |
| Trilauric | 33.90 |
| Trimyristin | 55.30 |
| Tripalmitin | 0.78 |
| Tristearin | 0.65 |
| Triarachidin | 0.73 |

The standard deviation of the major components are under 0.1%. Analysis of this reference standard is performed once each day, and results within two standard deviations are considered to demonstrate acceptable performance for the analysis.

2. Thin Layer Chromatography (TLC)

The extent of reaction progress in making propylene glycol diesters according to the present invention is monitored by thin layer chromatography (TLC) using high performance plates (Analtech HPTLC-GHLF 57527) and a solvent system comprising a mixture of reagent grade petroleum ether, ethyl ether and acetic acid (75:25:1 volume ratio). Developed plates are visualized by dipping in a mixture of reagent grade phosphomolybdic acid and methanol (5:95 weight ratio) and heating on a hot plate. Typical $R_f$ values with this procedure are as follows:

| Component | $R_f$ |
|---|---|
| Propylene glycol | 0.0 |
| Long chain monoesters | 0.22 |
| Fatty acids | 0.48 |
| ML/LM diesters | 0.80 |
| Fatty acid anhydrides | 0.86 |
| Unsaponifiables | 1.00 |

3. Fatty Acid Composition

The method for determining the fatty acid composition of the propylene glycol diesters according to the present invention is described in D'Alonzo et al, "Analysis of Processed Soy Oil By Gas Chromatography," *J. Am. Oil Chem. Soc.*, Vol. 58 (1981), pp. 215 et seq., and A.O.C.S. Official Analytical Methods, C3 1-62, Ce 1c-89.

4. Peak Melt Point, Heat of Fusion and Solids Content by Differential Scanning Calorimetry The principles of Differential Scanning Calorimetry (DSC) and its application to confections are described by Chapman, *J. Am. Oil Chem. Soc.*, Vol. 48 (1971), pp. 824 et seq. Details of DSC operation are described in a manual by Perkin-Elmer Corporation entitled "Instructions for Model DSC-4", (1987).

a. Preparation of Sample

A sample of the fat (propylene glycol diester or cocoa butter) is melted until clear on a hot water bath. Two to three grams of the melted sample is placed in a 10 ml. glass vial and then heated to a temperature of 145° F. (62.8° C.), and then held at this temperature for 30 minutes. The heated sample is then quickly chilled by immersion of the vial in a 50% water/50% ice bath, and then held in this bath for 15 minutes. After chilling, the cocoa butter samples are tempered at 38° F. (3.3° C.) for 48 hours and then placed in a 70° F. (21.1° C.) environment for an additional 48 hours prior to analysis. After chilling, the propylene glycol diester samples are placed in a 70° F. (21.1° C.) environment for a minimum of 48 hours prior to analysis.

b. Measurement

A Perkin-Elmer DSC-4 is used with a Thermal Analysis Data Station (TADS) 3600 software package that is capable of analyzing the thermogram to determine the peak melt point, heat of fusion and solids content of the sample. (The DSC is calibrated against an Indium reference standard and procedure supplied by Perkin-Elmer). Five mg. of the prepared sample is weighed into the sample pan. The sample is cooled to 0° C., maintained at 0° C. for 5 minutes, and then scanned from 0° C. to 50° C. at the rate of 2.5° C. per minutes. The peak melt point of the sample is the temperature at the highest point on the endothermic peak. The heat of fusion of the sample is determined by integrating the area under the endothermic peak. In determining the solids content of the sample, the thermogram is first normalized, and then the endothermic peak is bracketed: (1) at or just below the point of the base line deviation and below 10° C.; and (2) at or just above the point at which the thermogram returns to the base line and above 38° C. The percent solids content is then determined by integration of the thermogram between the bracketed points, and reporting the results at various temperatures (typically ten) covering the range of from 24° C. to 38° C.

G. Specific Illustrations of Propylene Glycol Diesters and Their Use in Chocolate-Flavored Products The following are specific illustrations of the preparation of propylene glycol diesters and their use in chocolate-flavored products according to the present invention:

EXAMPLE 1

To two 5 liter round-bottom glass reaction flasks fitted with agitator, 80° C. reflux condenser, and nitrogen sparge were added 669 and 591 grams, respectively, of USP grade 1,2-propylene glycol (Fisher). The propylene glycol in each flask was heated to 100° C. with a 1 liter/minute nitrogen sparge. To one of the flasks was added 850 grams of Jahres Fabrinker HF fatty acids having a typical fatty acid composition of 5% $C_{18:0}$, 36% $C_{20:0}$, 56% $C_{22:0}$, 3% $C_{24:0}$ (hereafter "HF reaction mixture"). To the other reaction flask was added 950 grams Jahres Fabrinker LF fatty acids having a typical fatty acid composition of 9% $C_{18:0}$, 43% $C_{20:0}$, 46% $C_{22:0}$, 2% $C_{24:0}$ (hereafter "LF reaction mixture"). Each of the flasks contained propylene glycol to fatty acids in a mole ratio of 3:1. After the HF and LF fatty acids were added, each of the reaction flasks were heated to 200° C. under total reflux for 20 hours until there was complete consumption of the HF and LF fatty acids, as determined by thin layer chromatography.

The crude reaction mixtures were allowed to cool to 110° C. The excess unreacted propylene glycol in each flask was vacuum stripped at 5 mm Hg using increasing temperatures up to 180° C., and then nitrogen sparged for 1 hour at 6 liters/minute. Removal of residual propylene glycol was verified by thin layer chromatography. The stripped HF reaction mixture contained 62.4% monoesters and 37.6% diesters, while the LF reaction mixture contained 58.3% monoesters and 41.7% diesters (propylene glycol free basis).

The stripped reaction mixtures were each distilled on a two-inch laboratory wiped film evaporator (Pope) at 200° C., 5 to 20 micron Hg pressure, 490 rpm reverse wiper speed, 80° C. internal condenser, and 5 drops/second flow rate. A 55% (initial feed weight basis) and 61.6% cut were made for the LF and HF reaction mixtures, respectively. The distillate from the LF reaction mixture contained 99.5% monoesters and 0.5% diesters, while the distillate from the HF reaction mixture contained 99.4% monoesters and 0.6% diesters. The monoesters in each distillate readily solidified to a creamy solid at ambient temperature.

To two 5 liter round-bottom glass reaction flasks fitted with vigorous agitation, 80° C. reflux condenser, and 7 liter/minute nitrogen sparge, were added 1679 grams (for the HF monoesters) and 1698 grams (for the LF monoesters) of caprylic ($C_8$) fatty acid (99% purity from Henkel), respectively. The HF and LF monoesters (500 grams each) in melted form (~100° C.) were added dropwise to the hot (190° C.) caprylic acid in the respective flasks over a 45 minute period. The reaction temperature in each flasks were increased to 200° C. for an additional 2 hours until conversion of all monoesters to diesters occurred, as determined by thin layer chromatography. The HF reaction mixture contained 1.4% MM, 96.3% ML/LM, and 2.3% LL diesters, while the LF reaction mixture contained 2.0% MM, 94.9% ML/LM, and 3.1% LL diesters. (As determined by CNP and reported on an acid-free basis, "MM"=$C_{16}$ to $C_{20}$, "ML/LM"=$C_{22}$ to $C_{34}$, and "LL"=$C_{36}$ to $C_{48}$).

The crude reaction mixtures were allowed to cool to 110° C., and then vacuum stripped at 3 to 5 mm Hg using increasing temperatures up to 170° C. and a nitrogen bubble tube. The stripped HF reaction mixture contained 1.9% MM, 95.0% ML/LM and 2.5% LL diesters, while the stripped LF reaction mixture contained 1.5% MM, 95.1% ML/LM, and 3.4% LL diesters. The residual fatty acid levels of the stripped HF and LF reaction mixtures were 5.1% and 5.5%, respectively.

Each reaction mixture was then stripped separately on a 2-inch Pope wiped film evaporator at 190° to 200° C., 5 to 30 micron pressure, 45° C. internal condenser, 500 rpm reverse wiper speed, and 4 to 5 drops/second flow rate. A 20.4% and 20.2% cut was made of the HF and LF mixtures, respectively. The stripped HF residue contained 96.9% ML/LM and 3.1% LL diesters, while the stripped LF residue contained 95.8% ML/LM and 4.2% LL diesters.

Each stripped residue was separately distilled on the Pope wiped film evaporator at 220° C., 5 to 15 micron pressure, 45° C. internal condenser, 500 rpm reverse wiper speed, and 4 drops/second flow rate. An 88.7% and 89.4% cut was made of the HF and LF residues, respectively. The HF distillate contained 98.6% ML/LM and 1.4% LL diesters, while the LF distillate contained 98.7% ML/LM and 1.3% LL diesters.

The HF and LF distillates were separately steam deodorized at 204° to 210° C. for 2 hours at 3 mm Hg pressure using 50 ml water as steam (~4%/hour), filtered and then combined in a 50:50 weight ratio to provide a propylene glycol diester composition containing 98.2% ML/LM and 1.4% LL diesters, and 0.4% unesterified fatty acids.

Figure 3:
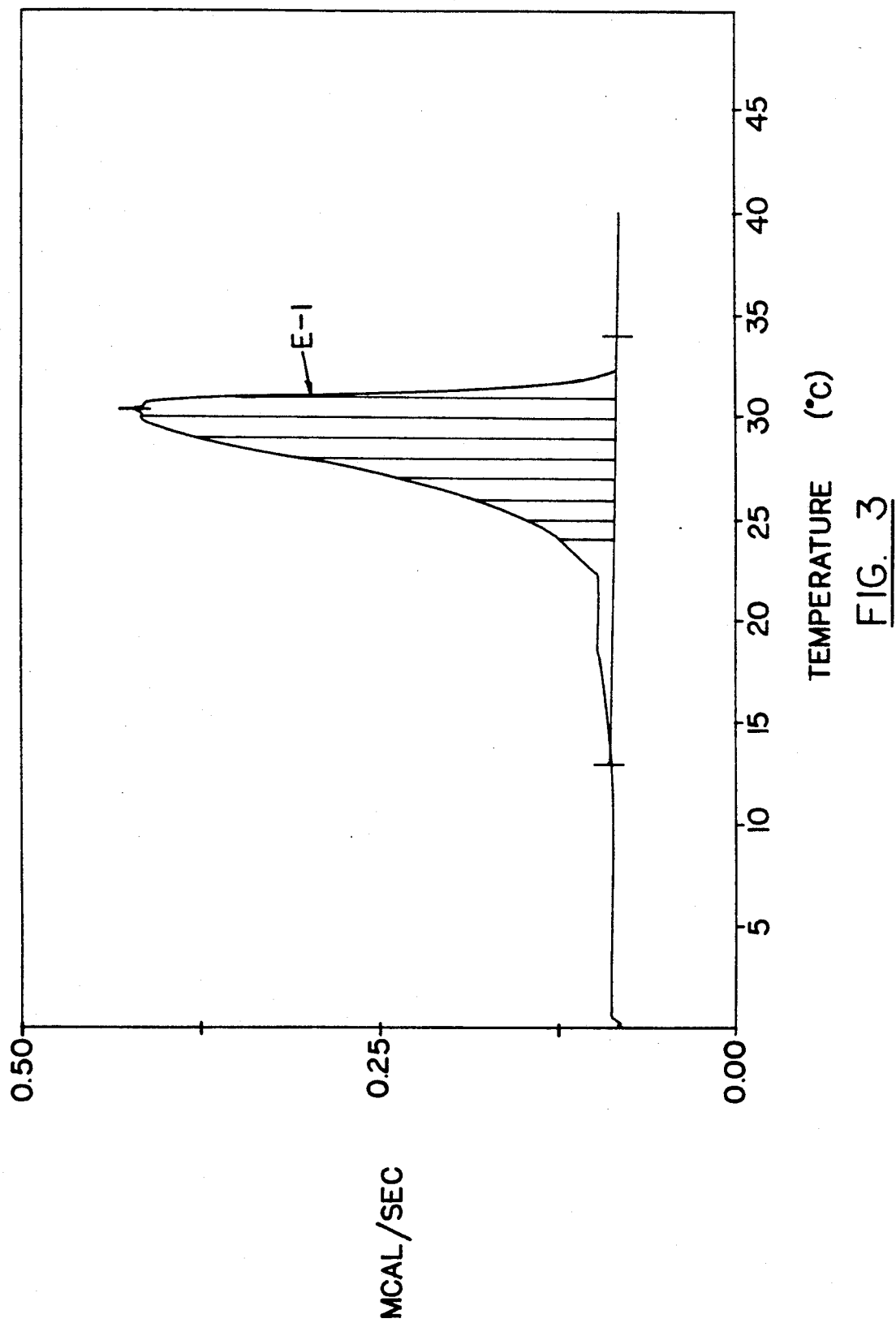
FIG. 3 is the thermogram obtained by DSC of the propylene glycol diester composition of Example 1.

The thermogram obtained by DSC for this propylene glycol diester composition is shown in FIG. 3 and has one endothermic peak E-1. The composition had a peak melt point of 30.3° C. and a heat fusion of 37.14 cal./gram. The solids content versus temperature of the composition is shown in FIG. 2 as curve P-5. The fatty acid composition was as follows:

| Fatty Acid | % |
| --- | --- |
| $C_{8:0}$ | 22.5 |
| $C_{10:0}$ | 0.1 |
| $C_{16:0}$ | 0.3 |
| $C_{18:0}$ | 4.0 |
| $C_{18:2}$ | 0.3 |
| $C_{20:0}$ | 27.5 |
| $C_{20:1}$ | 0.1 |
| $C_{21:0}$ | 1.2 |
| $C_{22:0}$ | 41.2 |
| $C_{22:1}$ | 0.2 |
| $C_{24:0}$ | 2.4 |

Based on the above fatty acid composition, an Iodine Value of 1.1 was calculated.

EXAMPLE 2

The diester composition of Example 1 was used in the following milk chocolate-flavored formulation:

| Ingredient | Percentage |
| --- | --- |
| Chocolate liquor (52% cocoa butter) | 1.50 |
| Cocoa powder (11% cocoa butter) | 6.90 |
| Whole fat milk solids (26% butterfat) | 5.96 |
| Non-fat milk solids (0.8% butterfat) | 6.20 |
| Vanillin | 0.05 |
| Lecithin | 0.30 |
| Sugar | 51.35 |
| Diester composition | 27.90 |

The formulation contained 31% total fat (89.9% from the diester composition, 5.0% from cocoa butter, and 5.1% from butterfat).

Other than the lecithin and diester composition, all of the above ingredients were combined together and thoroughly mixed in a jacketed Hobart mixer. About 70% melted diester composition was then added to this mixture and blended in. The blend was milled twice on a four-roll mill at 49° C. and 200 psi pressure. The milled blend was dry conched for 1 hour at 63° C. prior to addition of the remaining diester composition and a portion of the total lecithin. The dry conched mixture was then wet conched for about 16 hours at 63° C., after which the remaining lecithin was added and mixed well to reduce its viscosity.

Molded fully crystallized chocolate-flavored products were obtained from this wet-conched mixture by three methods. In the first method, the wet-conched mixture was cooled to 38° C., molded (plastic wafer mold), and then quick-cooled in a freezer (−23° C.) for 15 minutes. In the second method, the wet-conched mixture was cooled and then held at 27.5° C. for about 30 minutes, molded at 31° C., and then placed in a cooling chamber (3° C.) for a period of 15 minutes. In the third method, the wet-conched mixture was cooled to 29° C., and about 10% β' seed crystals (prepared by external ambient/slush crystallization of a separate chocolate-flavored mass) were then added. The seeded mixture was then held at 29° C. for about 10 minutes, molded at 31° C., and then placed in a cooling chamber (3° C.) for 15 minutes. The fully crystallized products prepared by each of these methods were characterized by rapid melt-away in the mouth, good mold contraction, high gloss, excellent snap, good chocolate flavor release, and a cooling sensation in the mouth during melting. These fully crystallized products also did not exhibit any bloom formation after 10 weeks at 21° C.

EXAMPLE 3

The diester composition of Example 1 was used in preparing milk chocolate-flavored products containing crystallization promoters and bloom inhibitors. In preparing these products, the milk chocolate-flavored formulation and preparation procedures described in Example 2 were used. Sorbitan monostearate (Grindsted Famodan MS) and palm stearine (Lodens Croklin Cote Hi) were melted at 60° C. into the diester composition, each at a level of 1% of the total formulation. The diester composition containing these melted-in additives was then conched with the remaining ingredients at 60° C. for 2 hours. Molded fully crystallized chocolate-flavored products were obtained from this conched mixture by two methods. In the first method, the conched mixture was cooled to 38° C., molded (plastic wafer molds), and then quick-cooled in a freezer (−23° C.) for 15 minutes. In the second method, the conched mixture was cooled to 38° C., cooled to and then held at 23° C. for 5 minutes, molded at 29° to 31° C., and then placed in a cooling chamber (3° C. or 10° C.), for a period of 15 minutes. The fully crystallized products prepared by each of these methods had good gloss, rapid melt-away in the mouth and good chocolate flavor release and did not exhibit any bloom formation after 10 weeks at 21° C.

Enrobed vanilla cookies were also prepared by using this milk chocolate-flavored formulation containing crystallization promoters and bloom inhibitors. These products were prepared by cooling the wet-conched mixture to 38° C., enrobing the cookies, and then quick-cooling the enrobed products in a freezer (−23° C.) for 15 minutes. The enrobed products had high gloss and did not exhibit any bloom formation after 10 weeks at 21° C.

EXAMPLE 4

The purified HF propylene glycol monoesters of Example 1 (99.5% monoesters and 0.5% diesters) were reacted with caprylic ($C_8$) anhydride (Sigma) at a 1.2:1 anhydride to monoester mole ratio at 140° C. for 1.75 hours under a nitrogen purge. Reaction completion was confirmed by thin layer chromatography. On completion, the reaction mixture contained 0.3% MM, 98.7% ML/LM, and 1.0% LL diesters.

The crude reaction mixture was purified by dissolving in 7 parts of a 95%/5% mixture of ethanol and methanol solvent at 45° C. The solution was cooled to 5° C., followed by filtration to recover the crystallized product which was then washed with solvent. The recovered propylene glycol diester composition was oven dried at 80° C. and contained 0.1% MM, 98.5% ML/LM, and 1.3% LL diesters. This propylene glycol diester composition was melted at 80° C., cooled to 40° C., and then molded into wafers. Wafers that were quick-cooled in a freezer (−23° C.) for 15 minutes and then warmed to 21° C. for 1 hour had an opaque, hard consistency and were composed of fine fat crystals. Wafers that were placed in a cooling chamber (3° C., 10° C. or 21° C.) for 15 minutes and then warmed to 21° C. for 1 hour had a clear, sticky consistency and hardened overnight as large, coarse crystals.

EXAMPLE 5

Propylene glycol monoesters (3% $C_{20:0}$, 93% $C_{22:0}$, 2% $C_{24:0}$) having a purity of 99.4% were esterified with an equimolar mixture of caprylic ($C_8$) and capric ($C_{10}$) fatty acids at mole ratios of fatty acids to monoesters of 1.5:1 (Reaction 5A), 4.5:1 (Reaction 5B), and 9:1 (Reaction 5C), respectively. The reactions were carried out at 200° C. in a three-necked round bottom flask with a 0.4 L./minute nitrogen sparge (to remove water), agitation, and refluxing (21° C. condenser). The reactions were monitored by thin layer chromatography until completion, i.e. conversion of all monoesters to diesters. The results of Reactions 5A through 5C are shown below:

| Reaction | Mole Ratio | Diester Composition* | | |
|---|---|---|---|---|
| | | MM | ML/LM | LL |
| 5A | 1.5:1 | 8.2% | 75.1% | 16.7% |
| 5B | 4.5:1 | 2.3% | 92.8% | 4.9% |
| 5C | 9:1 | 1.4% | 96.6% | 2.0% |

*by CNP, as in Example 1

The 5C reaction mixture was stripped of fatty acids under vacuum using progressively increasing temperatures of from 120° C. to 180° C., and then nitrogen sparged. The stripped reaction mixture was then solvent crystallized using 7 parts ethanol. The desired ML/LM fraction crystallized at 3° C., and was oven dried at 80° C. The resulting propylene glycol diester composition contained 99.4% ML/LM and 0.3% LL diesters, and 0.3% unesterified fatty acids.

Figure 4:
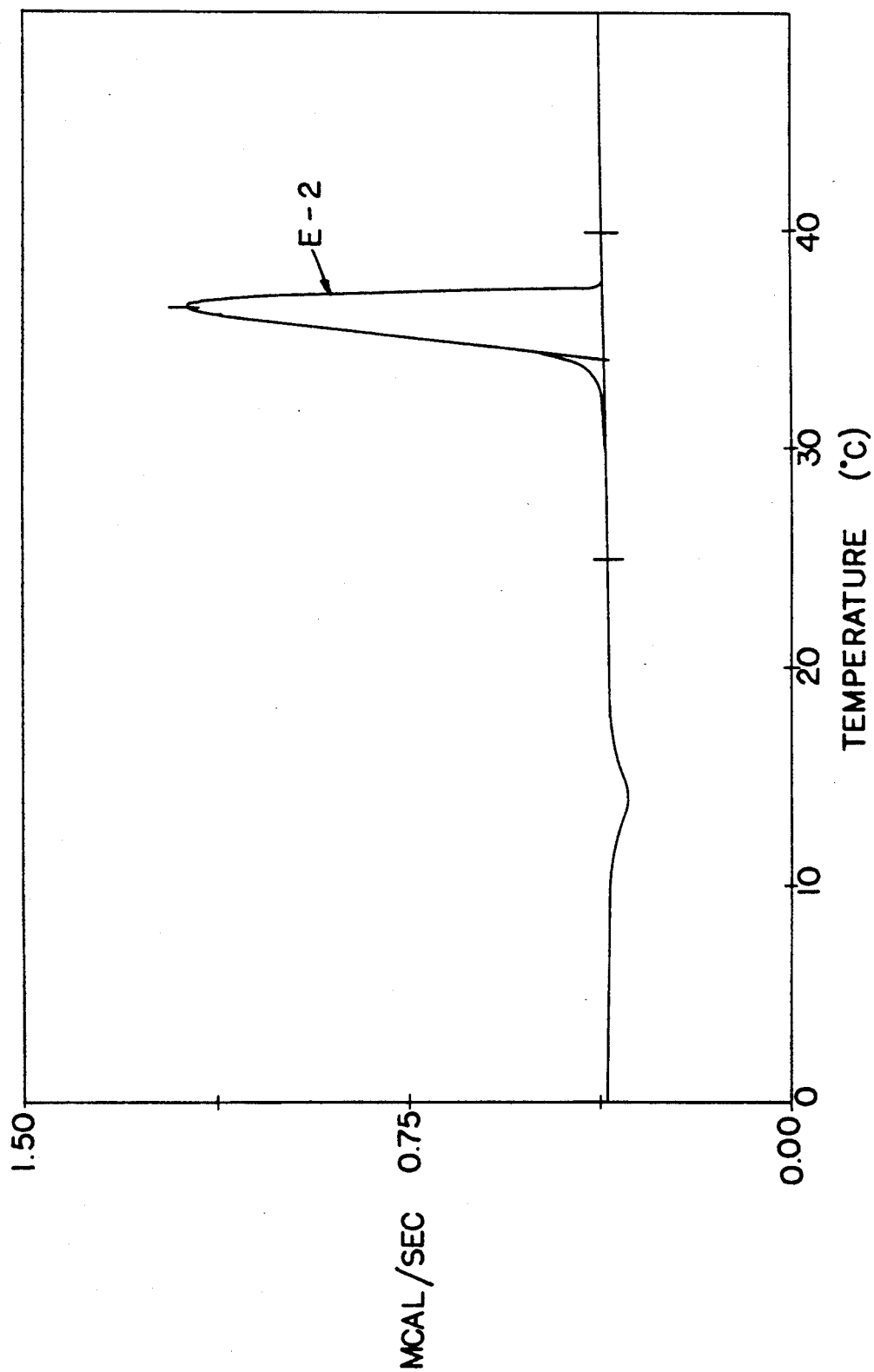
FIG. 4 is the thermogram obtained by DSC of the propylene glycol diester composition of Example 5C.

The thermogram obtained by DSC for this propylene glycol diester composition is shown in FIG. 4 and has one endothermic peak E-2. The composition had a peak melt point of 36.6° C. and a heat fusion of 40.4 cal./gram. The solids content versus temperature of the composition is shown in FIG. 2 as curve P-6.

EXAMPLE 6

Propylene glycol monoesters (7.2% $C_{20:0}$, 86.3% $C_{22:0}$, 2.7% $C_{24:0}$) having a purity of 98.9% were esterified with caprylic ($C_8$) acid (99% purity) at a fatty acid to monoester mole ratio of 9:1, with (Reaction 6A) and without (Reaction 6B) p-toluene sulfonic acid (PTSA) catalyst, and at a fatty acid to monoester mole ratio of 1.2:1, with (Reaction 6C) and without (Reaction 6D) PTSA catalyst. The reactions were carried out in a stirred three-neck round bottom flask with 0.1–0.2 L./min. nitrogen purge and ambient (21° C.) reflux condenser. The reactions were monitored by thin layer chromatography until complete conversion of monoester to diester. In the case of reaction 6B and 6D, the reaction mixtures were heated to 95° C. prior to the addition of 0.4% PTSA catalyst. The results of Reactions 6A through 6D are shown below:

| Reaction | Temp. (°C.) | Time (Hrs.) | Diester Composition* | | |
|---|---|---|---|---|---|
| | | | MM | ML/LM | LL |
| 6A | 200 | 2 | 2.0% | 94.5% | 3.5% |
| 6B | 180 | 1 | 4.1% | 92.7% | 3.2% |
| 6C | 200 | 11 | 4.1% | 75.1% | 20.8% |
| 6D | 200 | 6 | 5.6% | 75.9% | 18.5% |

*by CNP, as in Example 1

EXAMPLE 7

The propylene glycol monoesters of Example 6 were esterified with caprylic acid (99% purity) at a mole ratio of fatty acid to monoester of 9:1 using various techniques to remove water and minimize side reactions (7A through 7E). The reactions were carried out in a well-agitated glass reactor having an ambient (21° C.) reflux condenser. Reaction 7A was the control and was carried out with a nitrogen sparge ratio of 3.36 L./mn.-L. Reaction 7B was carried out at a high nitrogen sparge rate (33.6 L./mn.-L.), while reaction 7C was carried out without nitrogen sparging. Reaction 7D involved adding melted monoester (100° C.) to the melted fatty acid over a 45 minute period. Reaction 7E involved carrying out the reaction under a vacuum (200 mm Hg). The results of reactions 7A through 7E are shown below:

| Reaction | Temp. (°C.) | Time (Hrs.) | Diester Composition* | | | Acid Hydrolysis** |
|---|---|---|---|---|---|---|
| | | | MM | ML/LM | LL | |
| 7A | 200 | 2 | 2.0% | 94.5% | 3.5% | 4.8% |
| 7B | 185 | 3 | 0.8% | 95.3% | 3.9% | 5.5% |
| 7C | 200 | 3 | 5.8% | 88.4% | 5.8% | 11.3% |
| 7D | 200 | 2.75 | 1.2% | 96.4% | 2.4% | 4.3% |
| 7E | 200 | 2 | 2.1% | 94.3% | 3.6% | 5.6% |

*by CNP, as in Example 1
**combined $C_{20:0}$, $C_{22:0}$ and $C_{24:0}$ acid level in reaction mixture, relative to total level of these acids in starting monoester

What is claimed is:

1. A reduced calorie propylene glycol diester composition having a peak melt point of from about 27° to about 37° C. that crystallizes into a stable $\beta'$ solid form, and which comprises:
   (a) at least about 90% ML/LM propylene glycol diesters, up to about 10% MM propylene glycol diesters and up to about 10% LL propylene glycol diesters, wherein M are medium chain saturated fatty acid radicals selected from the group consisting of caprylic and capric fatty acid radicals and mixtures thereof, and wherein L are long chain saturated fatty acid radicals selected from the group consisting of arachidic, behenic and lignoceric fatty acid radicals and mixtures thereof;
   (b) said medium chain radicals comprising from 0 to 100% caprylic radicals and from 0 to 100% capric radicals; and
   (c) said long chain radicals comprising from about 30 to about 95% behenic radicals, from about 5 to about 70% arachidic radicals and from 0 to about 5% lignoceric radicals.

2. The composition of claim 1 wherein said medium chain radicals comprise from about 25 to 100% caprylic radicals and from 0 to about 75% capric radicals, and wherein said long chain radicals comprise from about 50 to about 90% behenic radicals, from about 10 to about 50% arachidic radicals, and from 0 to about 3% lignoceric radicals.

3. The composition of claim 2 which comprises at least about 95% ML/LM diesters, up to about 2.5% MM diesters, up to about 2.5% LL diesters, and about 1% or less unesterified $C_{20}$–$C_{24}$ saturated fatty acids.

4. The composition of claim 3 which comprises at least about 98% ML/LM diesters, up to about 1% MM diesters, up to about 1% LL diesters and about 0.5% or less of said unesterified $C_{20}$–$C_{24}$ acids.

5. The composition of claim 1 which has a peak melt point of from about 29° to about 35° C.

6. A flavored reduced calorie confectionery product which comprises:
 (A) a flavor-enhancing amount of a flavor component;
 (B) from about 25 to about 45% of a fat component comprising:
  (1) at least about 60% of a reduced calorie propylene glycol diester composition having a peak melt point of from about 27° to about 37° C. that crystallizes into a stable $\beta'$ solid form, and comprising:
   (a) at least about 90% ML/LM propylene glycol diesters, up to about 10% MM propylene glycol diesters and up to about 10% LL propylene glycol diesters, wherein M are medium chain saturated fatty acid radicals selected from the group consisting of caprylic and capric fatty acid radicals, and mixtures thereof, and wherein L are long chain saturated fatty acid radicals selected from the group consisting of arachidic, behenic, and lignoceric fatty acid radicals, and mixtures thereof;
   (b) said medium chain radicals comprising from 0 to 100% caprylic radicals and from 0 to 100% capric radicals; and
   (c) said long chain radicals comprising from about 30 to about 95% behenic radicals, from about 5 to about 70% arachidic radicals and from 0 to about 5% lignoceric radicals;
  (2) up to about 25% milkfat;
  (3) up to about 15% cocoa butter; and
 (C) from about 55 to about 75% other nonfat confectionery ingredients.

7. The product of claim 6 wherein said diester composition has a peak melt point of from about 29° to about 35° C.

8. The product of claim 6 wherein said medium chain radicals comprise from about 25 to 100% caprylic radicals and from 0 to about 75% capric radicals, and wherein said long chain radicals comprise from about 50 to about 90% behenic radicals, from about 10 to about 50% arachidic radicals and from 0 to about 3% lignoceric radicals.

9. The product of claim 6 wherein said diester composition comprises at least about 95% ML/LM diesters, up to about 2.5% MM diesters, up to about 2.5% LL diesters, and about 1% or less unesterified $C_{20}$–$C_{24}$ saturated fatty acids.

10. The product of claim 9 wherein said diester composition comprises at least about 98% ML/LM diesters, up to about 1% MM diesters, up to about 1% LL diesters, and about 0.5% or less of said unesterified $C_{20}$–$C_{24}$ acids.

11. The product of claim 6 wherein said fat component comprises at least about 80% of said diester composition.

12. The product of claim 11 wherein said fat component comprises at least about 85% of said diester composition, and from about 5 to about 10% cocoa butter.

13. The product of claim 12 wherein said fat component comprises from about 5 to about 10% milkfat.

14. The product of claim 11 which comprises from about 0.1 to about 25% of a chocolate-flavor component.

15. The product of claim 14 which comprises from about 35 to about 65% sugar.

16. The product of claim 15 which comprises from about 40 to about 55% sucrose.

17. The product of claim 14 which comprises an effective amount of a reduced calorie sweetener and from about 10 to about 60% of a reduced calorie bulking agent.

18. The product of claim 17 wherein said reduced calorie bulking agent is selected from the group consisting of polydextrose, and 5-C-hydroxymethyl hexose compounds and their derivatives.

19. The product of claim 11 wherein said fat component further comprises an effective amount of a crystallization promoter selected from the group consisting of tribehenin, palm oil stearine, completely hydrogenated or substantially completely hydrogenated high erucic acid rapeseed oil, sodium dipalmitate, diacetyl tartaric acid monoglycerides, and 2-oleic-1,3-dibehenin.

20. The product of claim 19 wherein said fat component further comprises an effective amount of a bloom inhibitor selected from the group consisting of sorbitan tristearate, sorbitan monostearate, sucrose mono- and diesters, lactylated mono- and diglycerides, ethoxylated sorbitan monostearate, ethoxylated sorbitan tristearate, and polyglycerol esters.

21. A process for preparing a flavored reduced calorie confectionery product, which comprises the steps of:
 (I) forming a fluid flavored confectionery mass which comprises:
  (A) a flavor-enhancing amount of a flavor component;
  (B) from about 25 to about 45% of a fat component comprising:
   (1) at least about 60% of a reduced calorie propylene glycol diester composition having a peak melt point of from about 27° to about 37° C. that crystallizes into a stable $\beta'$ solid form and comprising:
    (a) at least about 90% ML/LM propylene glycol diesters, up to about 10% MM propylene glycol diesters and up to about 10% LL propylene glycol diesters, wherein M are medium chain saturated fatty acid radicals selected from the group consisting of caprylic and capric fatty acid radicals, and mixtures thereof, and wherein L are long chain saturated fatty acid radicals selected from the group consisting of arachidic, behenic, and lignoceric fatty acid radicals, and mixtures thereof;
    (b) the medium chain radicals comprising from 0 to 100% caprylic radicals and from 0 to 100% capric radicals; and (c) the long chain radicals comprising from about 30 to about 95% behenic radicals, from about 5 to about 70% arachidic radicals and from about 0 to about 5% lignoceric radicals;

(2) up to about 25% milkfat;

(3) up to about 15% cocoa butter; and (C) from about 55 to about 75% other nonfat confectionery ingredients;

(II) quickly cooling the fluid mass of step (I) to a temperature of about 40° F. (4.4° C.) or less to form an effective amount of $\beta'$ seed crystals from a portion of the diester composition;

(III) holding the cooled mass of step (II) at a temperature of about 55° F. (12.8° C.) or less for a period of at least about 5 minutes; and (IV) warming the cooled mass of step (III) to a temperature of about 70° F. (21.1 C.) or higher to provide a flavored confectionery product wherein the diester composition is fully crystallized into the $\beta'$ phase.

22. The process of claim 21 wherein the diester composition has a peak melt point of from about 29° to about 35° C.

23. The process of claim 19 wherein the medium chain radicals comprise from about 25 to 100% caprylic radicals and from 0 to about 75% capric radicals, and wherein the long chain radicals comprise from about 50 to about 90% behenic radicals, from about 10 to about 50% arachidic radicals and from 0 to about 3% lignoceric radicals.

24. The process of claim 23 wherein the diester composition comprises at least about 95% ML/LM diesters, up to about 2.5% MM diesters, up to about 2.5% LL diesters, and about 1% or less unesterified $C_{20}$–$C_{24}$ saturated fatty acids.

25. The process of claim 24 wherein the diester composition comprises at least about 98% ML/LM diesters, up to about 1% MM diesters, up to about 1% LL diesters, and about 0.5% or less of the unesterified $C_{20}$–$C_{24}$ acids.

26. The process of claim 23 wherein the fat component comprises at least about 80% of the diester composition.

27. The process of claim 26 wherein the fat component comprises at least about 85% of the diester composition, and from about 5 to about 10% cocoa butter.

28. The process of claim 27 wherein the fat component comprises from about 5 to about 10% milkfat.

29. The process of claim 26 wherein the fluid mass of step (I) comprises from about 0.1 to about 25% of a chocolate-flavor component.

30. The process of claim 29 wherein the cooled mass of step (II) is held at a temperature of about 40° F. (4.4° C.) or less for a period of at least about 10 minutes during step (III).

31. A process for preparing a flavored reduced calorie confectionery product, which comprises the steps of:

(I) forming a fluid flavored confectionery mass which comprises:

(A) a flavor-enhancing amount of a flavor component;

(B) from about 25 to about 45% of a fat component comprising:

(1) at least about 60% of a reduced calorie propylene glycol diester composition having a peak melt point of from about 27° to about 37° C. that crystallizes into a stable $\beta'$ solid form and comprising:

(a) at least about 90% ML/LM propylene glycol diesters, up to about 10% MM propylene glycol diesters and up to about 10% LL propylene glycol diesters, wherein M are medium chain saturated fatty acid radicals selected from the group consisting of caprylic and capric fatty acid radicals, and mixtures thereof, and wherein L are long chain saturated fatty acid radicals selected from the group consisting of arachidic, behenic, and lignoceric fatty acid radicals, and mixtures thereof;

(b) the medium chain radicals comprising from 0 to 100% caprylic radicals and from 0 to 100% capric radicals; and (c) the long chain radicals comprising from about 30 to about 95% behenic radicals, from about 5 to about 70% arachidic radicals and from about 0 to about 5% lignoceric radicals;

(2) up to about 25% milkfat;

(3) up to about 15% cocoa butter; and (C) from about 55 to about 75% other nonfat confectionery ingredients;

(II) holding the fluid mass of step (I) at a temperature of from about 78° to about 83° F. (from about 25.6° to about 28.3° C.) for a period of at least about 10 minutes to form an effective amount of $\beta'$ seed crystals from a portion of the diester composition;

(III) cooling the fluid mass of step (II) to a temperature of about 50° F. (10° C.) or less for a period of at least about 15 minutes; and (IV) warming the cooled mass of step (III) to a temperature of about 70° F. (21.1° C.) or higher to provide a flavored confectionery product wherein the diester composition is fully crystallized into the $\beta'$ phase.

32. The process of claim 31 wherein the diester composition has a peak melt point of from about 29° to about 35° C.

33. The process of claim 31 wherein the medium chain radicals comprise from about 25 to 100% caprylic radicals and from 0 to about 75% capric radicals, and wherein the long chain radicals comprise from about 50 to about 90% behenic radicals, from about 10 to about 50% arachidic radicals and from 0 to about 3% lignoceric radicals.

34. The process of claim 33 wherein the diester composition comprises at least about 95% ML/LM diesters, up to about 2.5% MM diesters, up to about 2.5% LL diesters, and about 1% or less unesterified $C_{20}$–$C_{24}$ saturated fatty acids.

35. The process of claim 34 wherein the diester composition comprises at least about 98% ML/LM diesters, up to about 1% MM diesters, up to about 1% LL diesters, and about 0.5% or less of the unesterified $C_{20}$–$C_{24}$ acids.

36. The process of claim 33 wherein the fat component comprises at least about 80% of the diester composition.

37. The process of claim 36 wherein the fat component comprises at least about 85% of the diester composition, and from about 5 to about 10% cocoa butter.

38. The process of claim 37 wherein the fat component comprises from about 5 to about 10% milkfat.

39. The process of claim 36 wherein the fluid mass of step (I) comprises from about 0.1 to about 25% of a chocolate-flavor component.

40. The process of claim 39 wherein the fluid mass of step (I) is held during step (II) for a period of from about 15 to about 45 minutes.

41. The process of claim 40 wherein the fluid mass of step (II) is cooled to a temperature of about 40° F. (4.4° C.) or less for a period of at least about 15 minutes during step (III).

42. The process of claim 31 wherein the cooled mass of step (II) is heated prior to step (III) to a temperature of from about 84° to about 95° F. (from about 28.8° to about 35° C.) to melt some, but not all, of the $\beta'$ seed crystals of the diester composition.

* * * * *